US008802164B2

(12) United States Patent
Shimoda et al.

(10) Patent No.: US 8,802,164 B2
(45) Date of Patent: Aug. 12, 2014

(54) METHOD FOR PROMOTING CARNITINE PALMITOYLTRANSFERASE ACTIVITY USING GREEN COFFEE BEAN EXTRACT

(75) Inventors: Hiroshi Shimoda, Aichi (JP); Michio Aitani, Aichi (JP); Tomoko Sugishita, Aichi (JP); Tadashi Okada, Aichi (JP); Hiromichi Murai, Aichi (JP); Emi Yamada, Aichi (JP)

(73) Assignee: Oryza Oil & Fat Chemical Co., Ltd., Aichi (JP)

( * ) Notice: Subject to any disclaimer, the term of this patent is extended or adjusted under 35 U.S.C. 154(b) by 205 days.

(21) Appl. No.: 13/038,513

(22) Filed: Mar. 2, 2011
(Under 37 CFR 1.47)

(65) Prior Publication Data
US 2011/0189313 A1 Aug. 4, 2011

Related U.S. Application Data

(63) Continuation of application No. 10/569,970, filed as application No. PCT/JP2004/014622 on Oct. 5, 2004, now abandoned.

(30) Foreign Application Priority Data

Oct. 6, 2003 (JP) .................................. 2003-346446

(51) Int. Cl.
*A61K 36/74* (2006.01)
(52) U.S. Cl.
USPC ........................................................ 424/731
(58) Field of Classification Search
USPC ................................................. 424/731, 725
See application file for complete search history.

(56) References Cited

U.S. PATENT DOCUMENTS 4,798,732 A * 1/1989 Osawa .......................... 426/542

FOREIGN PATENT DOCUMENTS

| EP | 0 714 968 A2 * | 5/1996 | ............. C09K 15/34 |
| JP | 62-111671 | 5/1987 | |
| JP | 4-145048 | 5/1992 | |
| JP | 4-145049 | 5/1992 | |
| JP | 11-246427 | 9/1999 | |

(Continued)

OTHER PUBLICATIONS

Natella et al. Coffee Drinking Influences Plasma Antioxidant Capacity in Humans. Journal of Agricultural Food and Chemistry. 2002. 50, 6211-6216.*

(Continued)

*Primary Examiner* — Patricia Leith
(74) *Attorney, Agent, or Firm* — Clark & Brody

(57) ABSTRACT

(PROBLEMS) To provide a highly safe dietetic composition originating in green coffee beans by which excellent dietetic effects can be obtained and which contributes to the prevention and treatment of life style-related diseases such as diabetes. (MEANS FOR SOLVING PROBLEMS) A dietetic composition characterized by comprising, as the active ingredient, a polar solvent extract of defatted green coffee beans. It is preferable that the above-described polar solvent extract is an extract obtained by using water-containing ethanol, still preferably water-containing ethanol having an ethanol concentration of from 40 to 90% (wt/wt). It is preferable that the above-described defatted green coffee beans are those obtained by extracting green coffee beans with N-hexane to thereby separate oily components therefrom. It is recommended to combine the above-described dietetic composition with one or more members selected from among *salacia* extract, evening primrose extract, sesamine and *garcinia*. This dietetic composition is usable as a material for foods, drinks, drugs, or skin preparations for external use.

19 Claims, 10 Drawing Sheets

(56) References Cited

FOREIGN PATENT DOCUMENTS

| | | | | |
|---|---|---|---|---|
| JP | 2000-309533 | 11/2000 | | |
| JP | 2000-333640 | 12/2000 | | |
| JP | 2001-321126 | 11/2001 | | |
| JP | 2002-281940 | 10/2002 | | |
| JP | 2002-308766 | 10/2002 | | |
| JP | 2002-316938 | 10/2002 | | |
| JP | 2003-12529 | 1/2003 | | |
| JP | 2003-34636 | 2/2003 | | |
| JP | 2003-160483 | 6/2003 | | |
| WO | WO 00/18416 | * | 4/2000 | ............. A61K 35/78 |
| WO | 02/09734 | 2/2002 | | |

OTHER PUBLICATIONS

American Journal of Pharmacy. vol. 29. 1857. p. 399.*

S. Kumar et al., "Phenolic Acids as Potential Inhibitors of Plant Amylase", *Current Science*, Aug. 5, 1982, vol. 51, No. 15, p. 739-742.

S. Rohn et al., "Inhibitory Effects of Plant Phenols on the Activity of Selected Enzymes", *Agricultural and Food Chemistry*, 2002, vol. 50, No. 12, p. 3566-3571, Fig. 1.2.

M. Karamac et al., "Inhibition of Pancreatic Lipase by Phenolic Acids—Examination in vitro", *Zeitschrift fuer Naturforchung* 1996, vol. 51, No. 11/12, p. 903-905, Figure 3.

R. Marett et al., "Long Term Supplementation of Arabinogalactan in Humans and its Effects on Blood Lipids, Glucose, and Insulin", *FASEB Journal* 2001, vol. 25, No. 4, p. A259-230.7.

L Difrancesco et al., "Effects of Soluble Fiber Extracted From Coffee on Plasma Lipids in Gerbils", *FASEB Journal* 1995, vol. 9, No. 4, p. A727-4216.

J. Shani et al., "Hypoglycaemic Effect of *Trigonella Foenum Graecum* and *Lupinus Termis* (Leguminosae) Seeds and their Major Alkaloids in Alloxan0Diabetic and Normal Rats", *Arch. Int. Pharmacodyn.* 210, 27-37 (1974).

C. De Maria et al., "Composition of green coffee fractions and their contribution to the volatile profile formed during roasting", *Food Chemistry* 50, (1994) 141-145.

L. Tholon et al., "An in vitro, ex vivo, and in vivo demonstration of the lipolytic effect onf slimming liposomes: An unexpected $\alpha_2$-adrenergic antagonism", *J. Cosmet. Sci.*, 53, 209-218, Jul./Aug. 2002.

* cited by examiner n=7, average value ± standard error, Significant difference* :p<0.05(Dunnett multiple comparative assay (n=6, average value ± standard error, Significant difference** :p<0.01(Dunnett multiple comparative assay)

A) Triglyceride accumulation

B) GPDH activity (n=6-7, Average value ± standard error)

(n=6-7, Average value ± standard error, significant difference**: p<0.01 (Dunnett multiple comparative assay)

(n = 4-5, Average value ± standard error, *:p<0.05)

[n = 6, Average value ± standard error, significant difference **:p<0.01(Dunnett multiple comparative assay)]

METHOD FOR PROMOTING CARNITINE PALMITOYLTRANSFERASE ACTIVITY USING GREEN COFFEE BEAN EXTRACT

FIELD OF THE INVENTION

This invention relates to a dietetic composition derived from green coffee beans and is applicable for ingredients of food and drink, medicines, cosmetics, or the like.

Obesity is caused by excessive eating, insufficient exercise or the like, and is considered as a risk factor for lifestyle-related diseases typically seen in diabetic persons. The total number of diabetic patients and people standing a good chance of developing diabetes is increasing yearly.

As dietetic substances, capsaicin to enhance fat metabolism, chitosan to reduce fat absorption, *citrus aurantium* to enhance lipolysis and others are already known. The above dietetic substances are now used for food or the like to support slimming for the purpose of beautification such as cellulite reduction, excess body water extraction, body fat reduction or the like. However, some of the above dietetic substances are not sufficient to achieve a dietary effect. Therefore, high-value added dietetic substances for treatment or prevention of the lifestyle-related diseases are now highly demanded in the market.

Prior arts concerning dietetic substances are disclosed in the following publications:
Publication of application 1: JP2003-34636
Publication of application 2: JP2002-308766
Nonpatent literature 1: Tholon L, et al., An in vitro, ex vivo, and vivo demonstration of the lipolytic effect slimming liposomes: An unexpected alpha(2)-adrenergic antagonism. J. Cosmet. Sci. 53, 209-18 (2002)

DISCLOSURE OF THE INVENTION

Problems to be Resolved by the Invention

In such circumstance as described above, the inventors researched contained components, contained amount, SOD mimicking activity, and others regarding extracts derived from various plants. It was found that green coffee beans contain plenty of chlorogenic acids and caffeine. After conducting various experiments, it was found that an extract derived from green coffee beans, especially a polar solvent extract derived from defatted green coffee beans contain dietetically effective components. Furthermore, as a novel bioactivity of extract derived from green coffee beans, fat absorption suppressing activity, carnitine palmitoyltransferase activity promoting action in connection with fat burning metabolism, and α-glucosidase activity inhibiting activity in connection with control of blood sugar level were all found and resulted in this invention.

This invention provides a highly safe dietetic composition, fat absorption suppressive composition, pancreatic lipase activity inhibiting composition, carnitine palmitoyltransferase activity promoting composition and α-glucosidase activity inhibiting composition derived from green coffee beans.

Also, this invention provides a dietetic food and drink, medicine, and dermatological preparation derived from green coffee beans.

Furthermore, this invention provides green-coffee-beans-derived food and drink and medicines comprising a fat absorption inhibitory action, pancreatic lipase activity inhibitory action, carnitine palmitoyltransferase promoting activity or α-glucosidase activity inhibitory action.

(Invention 1)

A dietetic composition in this invention to resolve the above problems is characterized by comprising a polar solvent extract derived from defatted green coffee beans.

And, a dietetic composition in this invention is characterized in that the aforementioned polar solvent extract is a hydroethanol extract.

Also, a dietetic composition in this invention is characterized in that the aforementioned solar solvent extract has an ethanol concentration of 40 to 90% (wt/wt).

Moreover, a dietetic composition in this invention is characterized in that the oil of the aforementioned green coffee beans is extracted and separated with N-hexane.

Furthermore, a dietetic composition in this invention is characterized in that one or more substances selected from among *salacia* extract, evening primrose extract, sesamine, and *garcia* is added to any of the aforementioned compositions.

Obesity is likely caused by excessive amounts of fat that stay in the fat metabolic pathway in the body. (See FIG. 11) Therefore, to prevent or treat the obesity caused by fat, the following diet programs should be effectively done.
Suppression of fat absorption,
Inhibition of fat accumulation
Enhancement of lipolysis, and
Enhancement of fat burning In this invention (Invention 1), an excellent and highly-safe diet-promoting composition can be derived from green coffee beans, and the effect on the above programs (1) to (4) can be entirely obtained in a balanced manner. Thus, the weight gain by taking fat into the body can be prevented, and the effective diet can be done.

Referring now to the aforementioned Publications 1 and 2, a medicine for improving lipid metabolism focused on a function of chlorogenic acid contained in the coffee beans is disclosed in Publication 1 and another different medicine for preventing and improving lifestyle-related diseases is disclosed in Publication 2. And it is disclosed in common that an extract derived from green coffee beans contains an anti-obesity effect.

However, a dietetic composition in the present invention is a highly-concentrated bioactive composition containing chlorogenic acid derived from green coffee beans after extracting "defatted green coffee beans" with the solar solvent, and is different from the composition obtained simply by extracting the green coffee beans. And, the polar solvent extract derived from the defatted green coffee beans contains plenty of excellent diet-promoting composition as well as chrologenic acid. Therefore, compared to the extract derived from non-defatted green coffee beans, a good effect of diet (weight-reducing effect) can be expected in the present invention. (See Groups 3 and 4 in Chart 9, Example 5 of the Publication 1). In the polar solvent extract derived from the green coffee beans in the present invention, such an excellent weigh-reducing effect can be more expected than in other cases which are done by simply taking the chlorogenic acid into the body. Such an excellent effect is a unique effect which can not be predicted in the Publications 1, 2 and others.

(Inventions 2 and 3)

A composition for inhibiting fat absorption in this invention (Invention 2) is characterized by comprising an extract as an active substance derived from the green coffee beans.

Also, a composition for inhibiting fat absorption in this invention (Invention 2) is characterized in that the aforementioned extract derived from the green coffee beans is a solar solvent extract derived from the defatted green coffee beans.

In addition, a composition for inhibiting fat absorption in this invention (Invention 2) is characterized in that the aforementioned solar solvent extract contains a hydroethanol extract.

Moreover, a composition for inhibiting fat absorption in this invention (Invention 2) is characterized in that the aforementioned polar solvent extract is a hydroethanol having an ethanol concentration of 40 to 90% (wt/wt).

Furthermore, a composition for inhibiting fat absorption in this invention (Invention 2) is characterized in that the oil of the aforementioned green coffee beans is extracted and separated with N-hexane.

A composition for inhibiting a pancreatic lipase activity in this invention (Invention 3) is characterized by comprising an extract as an active substance derived from green coffee beans.

Also, a composition for inhibiting a pancreatic lipase activity in this invention (Invention 3) is characterized in that the aforementioned extract derived from the green coffee beans is a solar solvent extract derived from the defatted green coffee beans.

In addition, a composition for inhibiting a pancreatic lipase activity in this invention (Invention 3) is characterized in that the aforementioned solar solvent extract contains a hydroethanol extract.

Moreover, a composition for inhibiting a pancreatic lipase activity in this invention (Invention 2) is characterized in that the aforementioned polar solvent extract is a hydroethanol having an ethanol concentration of 40 to 90% (wt/wt).

Furthermore, a composition for inhibiting a pancreatic lipase activity in this invention (Invention 3) is characterized in that the oil content of the aforementioned green coffee beans is extracted and separated with N-hexane.

As described above, when determining the diet effect focusing on fat, normally one of the following effects on the fat metabolism pathway is reviewed; (1) suppression of fat absorption, (2) inhibition of fat accumulation (3) enhancement of lipolysis, and (4) enhancement of fat burning. The aforementioned Publications 1 and 2 teach the lipolysis promoting effect indicated by measuring the amount of triglycerol, and also suggests an anti-obesity effect contained in the green coffee beans. However, it is little known that the extract derived from the green coffee beans has a fat absorption suppressive effect when the fat is taken into the body.

In the experiments conducted by the inventors, bioactivity of the extract derived from the green coffee beans was tested in the fat absorption system of the lipolysis, and then the pancreatic lipase inhibitory action relating to the fat absorption suppressive action and fat absorption metabolism was found. Thus, in this invention, the diet effect can be improved in terms of the fat absorption suppressive effect by the extract derived from the green coffee beans (Invention 2) and the pancreatic lipase inhibitory effect (Invention 3). In other words, a dietetic composition including the extract, such as active substances for suppressing fat absorption or inhibiting pancreatic lipase action, derived from the green coffee beans can be provided in this invention. And the polar solvent extract (including ethanol extract and N-hexane defatted substance) derived from the defatted green coffee beans described in the above Inventions 2 and 3 can be used for the active substances for effect.

(Invention 4)

A composition for promoting a carnitine palmitoyltransferase activity in this invention (Invention 4) is characterized by comprising an extract as an active substance derived from green coffee beans.

Also, a composition for promoting a carnitine palmitoyltransferase activity in this invention (Invention 4) is characterized in that the aforementioned extract derived from the green coffee beans is a solar solvent extract derived from the defatted green coffee beans.

In addition, a composition for promoting a carnitine palmitoyltransferase activity in this invention (Invention 4) is characterized in that the aforementioned solar solvent extract contains a hydroethanol extract.

Moreover, a composition for promoting a carnitine palmitoyltransferase activity in this invention (Invention 4) is characterized in that the aforementioned polar solvent extract is a hydroethanol having an ethanol concentration of 40 to 90% (wt/wt).

Furthermore, a composition for promoting a carnitine palmitoyltransferase activity in this invention (Invention 4) is characterized in that the oil of the aforementioned green coffee beans is extracted and separated with N-hexane.

A brown adipose tissue related to the fat metabolism is one of fat-burning tissues which can convert energy to heat and burn it off. It is known that heat production is done on a membrane of the brown adipose tissue mitochondria and a special uncoupling protein (UCP-1) functions the heat conversion.

It is reported that the caffeine contained in the green coffee beans has a promoting effect of the UCP-1 expression of the brown adipose tissue of diabetic mice. As a result, it is contemplated that the green coffee beans containing caffeine function to burn and consume the fat producing heat.

On the other hand, the fatty acid degraded and separated from the adipose tissue is partially delivered into the liver and metabolized by β-oxidation in the mitochondria of the hepatic cell. When the fatty acid is delivered into the mitochondria, the carnitine and a transfer enzyme like carnitine palmitoyltransferase (CPT) function and both are on the rate-limiting step of the β-oxidation.

The Publication 1 teaches that chrologenic acids contained in the green coffee beans activate a gene transcription of the enzyme which is important to the fatty acid metabolism of the β-oxidation. However, it does not teach any effects on the activity of the enzyme itself by the chlorogenic acids.

In the experiments conducted by the inventors, the bioactivity of the extract derived from the green coffee beans was tested in the fat burning system of the fat metabolism, and a stimulatory effect of carnitine palmitoyltransferase (CPT) relating to the β-oxidation has been finally found. Thus, in this invention (Invention 4), the diet effect can be improved in terms of the fat burning promoting effect by activating the carnitine palmitoyltransferase (CPT). In other words, the dietetic composition including extracts such as active substances for promoting the carnitine palmitoyltransferase that are derived from the green coffee beans can be provided in this invention. And as an active substance for promoting the carnitine palmitoyltransferase (CPT), the polar solvent extract (including the ethanol extract and the N-hexane defatted substance) derived from the defatted green coffee beans described in the above Invention 4 can be used for the active substances for effect.

(Invention 5)

A composition for inhibiting an α-glucosidase activity in this invention (Invention 5) is characterized by comprising the extract as the active substance derived from the aforementioned green coffee beans.

Also, a composition for inhibiting the α-glucosidase activity in this invention (Invention 5) is characterized in that the aforementioned extract derived from the green coffee beans is a solar solvent extract derived from the defatted green coffee beans.

In addition, a composition for inhibiting the α-glucosidase activity in this invention (Invention 5) is characterized in that the aforementioned solar solvent extract contains a hydroethanol extract.

Moreover, a composition for promoting the α-glucosidase activity in this invention (Invention 5) is characterized in that the aforementioned polar solvent extract is a hydroethanol having an ethanol concentration of 40 to 90% (wt/wt).

Furthermore, a composition for inhibiting the α-glucosidase activity in this invention (Invention 5) is characterized in that the oil of the aforementioned green coffee beans is extracted and separated with N-hexane.

In the test of the bioactivity of glycolytic enzyme, such as α-amylase, α-glucosidase or the like, derived from the green coffee beans, it was found that the extract derived from the green coffee beans has an excellent inhibitory effect especially in regard to the α-glucosidase. Thus, in this invention (Invention 5), α-glucosidase enzyme activity is inhibited so that postprandial elevation of blood glucose levels can be suppressed and the diabetes and obesity can be finally prevented. In other words, this invention provides an anti-diabetic composition or dietetic composition containing an extract derived from the green coffee beans, as an active substance for inhibiting α-glucosidase activity. And as an active substance for inhibiting α-glucosidase activity, the polar solvent extract (including ethanol extract and N-hexane defatted substance) which is derived from the defatted green coffee beans described in the above Invention 5 can be used for the active substances for effects.

DETAILED DESCRIPTION OF THE PREFERRED EXAMPLES

Figure 1:
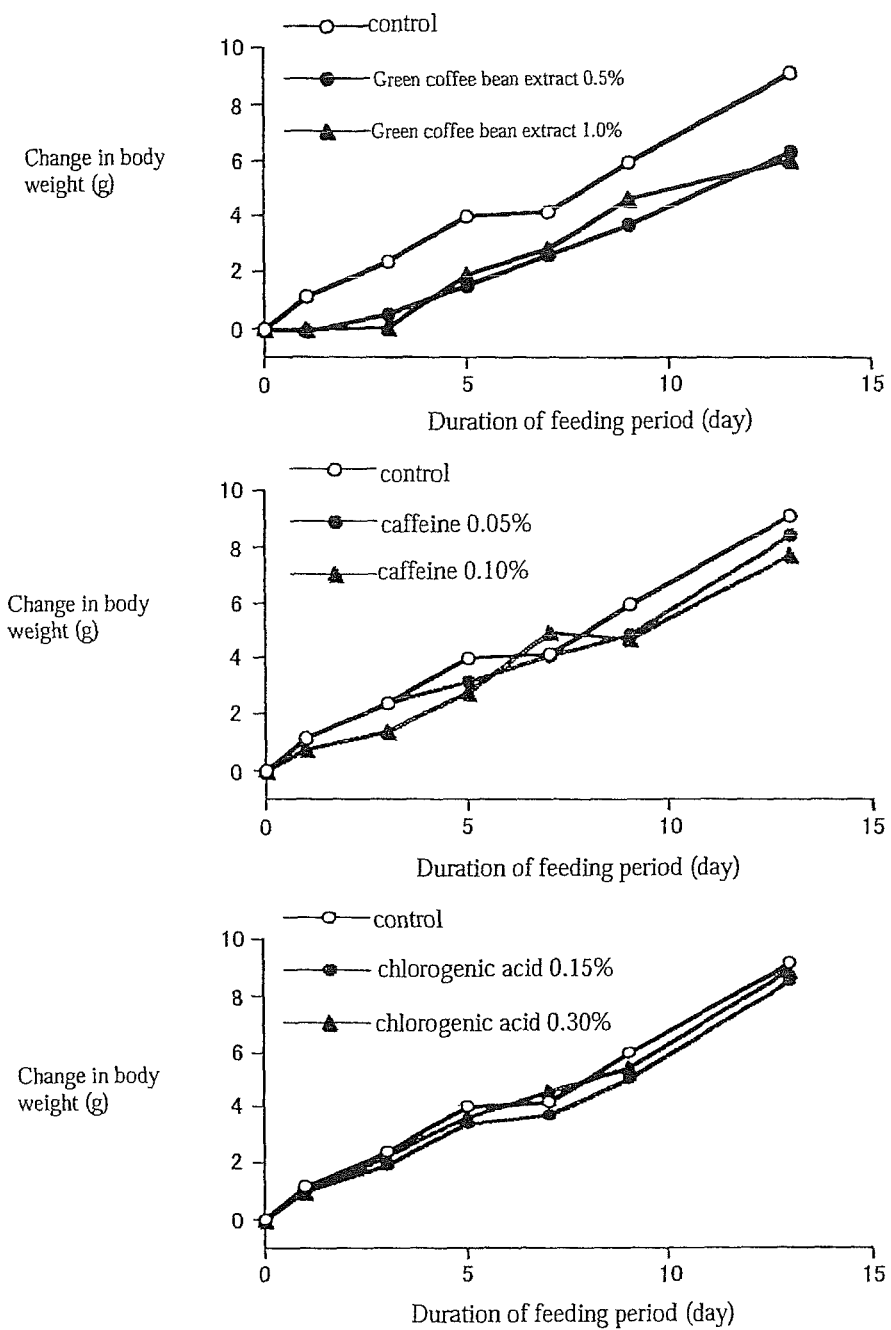
FIG. 1 is a graph showing an effect on the weight gain of mice which continuously take an extract derived from the green coffee beans and substances derived from coffee beans (caffeine and chlorogenic acid).

An example of the dietetic composition in this invention (Invention 1) is here described. Invention 1 is applicable similarly with Invention 2 (a composition for suppressing fat absorption), Invention 3 (a composition for inhibiting pancreatic lipase activity), Invention 4 (a composition for promoting carnitine palmitoyltransferase activity) and Invention 5 (a composition for inhibiting α-glucosidase activity).

In this invention, the green coffee beans, which are used as a basic ingredient to produce a dietetic composition, are the same used to brew coffee. The coffee beans used brewing coffee are normally roasted for approx. 15 minutes at the maximum temperature of 200 to 215° C. However, green coffee beans not roasted coffee beans are used in this invention.

The coffee tree, a rubiaceous evergreen shrub of Ethiopian origin produces the ingredient used in this invention. Normally, each coffee berry has two beans (seeds) inside. Each bean (seed) is of a hemispheric shape and has a deep vallecula on its flat surface. The Arabian coffee tree (*Coffea Arabica* L.), the Congolese coffee tree (*C. robusta* Linden), Land the Liberian coffee tree (*C. liberica* Bull), or others are widely cultivated. In this invention, the type of coffee bean or where it is grown (rabica, robusta, or the like) is not specified.

To prepare the coffee beans for beverage use, there are two methods used: the dry process and the wet process. In the dry process, the coffee berries are first dried, then the dried flesh and outer covering of the coffee beans are removed. In the wet process, the coffee berries are first soaked in water, then the flesh and outer covering of the coffee beans are fermented and dried, they are simply removed. In this invention, either on of the above methods can be used.

Defatted green coffee beans are preferably used for extracting the ingredients needed for the inventive dietetic composition used in this invention. After removing the oil from the green coffee beans, the dietetically functioning substances can easily be extracted with solvent. To defat the green coffee beans, it is preferable to first compress the green coffee beans to remove the oil. Then, to extract and separate the remaining oil from the compressed cake to use the defatting solvent, lipophilic organic solvent. Also, when the aforementioned Inventions 2 to 5 are put into practice, non-defatted green coffee beans can be used. For example, it is also possible to crush the green coffee beans and to extract the active substances from the crushed beans with solvent.

An N-hexane, acetone or the like can preferably be used for the defatting solvent. If the N-hexane is especially used as a defatting solvent, the extracted oil can be used for an edible oil, and the extract derived from the defatted green coffee beans can easily be used for food materials.

To extract the dietetically functioning ingredients from the defatted green coffee beans, solar solvents such as water, methanol, ethanol, isopropyl alcohol, 1,3-butylene glycol, ethylene glycol, propylene glycol, glycerin, ethyl acetate, or the like can be used. Two or more solvents described above can be mixed.

If the water and ethanol are preferably mixed and used as an extracting solvent, the active substances are efficiently extracted. Particularly, the action of the active substance is not easily lowered by the hydroethanol when being extracted. Thus, hydroethanol is a preferable extracting solvent since the extract can safely be used for food. The type of water used for extracting process is not specified. Tap water, distilled water, mineral water, ionized alkaline water, deep water or the like can be used. Also, the active substances can be extracted by using a non-polar solvent (acetone or the like when practicing the above Inventions 2 to 5.

If the hydroethanol is used for extracting the dietetically functioning ingredients from the defatted coffee beans, the extraction temperature should be from 20 to 80° C., preferably from 40 to 50° C. If the extraction temperature is too low, the active substances will not easily be extracted, and if the temperature is too high, the activity of the active substances will easily be reduced.

The extracting solvent is a hydroethanol which has an ethanol concentration of 40 to 90% (wt/wt), preferably the concentration of 60 to 80% (wt/wt). The reason why the ethanol concentration should be 40% (wt/wt) or more is that if the ethanol content is too low, the active substance will not sufficiently be extracted. Also the reason why the ethanol concentration should be 90% (wt/wt) or less is that if the ethanol content is too high, the remaining oil of the defatted green coffee beans will easily be leached into the hydroethanol. It is preferable to repeat the hydroethanol extractions, with changes in the ethanol concentration as needed, so that the content rate of the active substance will increase.

To extract the dietetically functioning ingredients, continuous extraction, soaking extraction, countercurrent extraction, supercritical extraction, or the like can also be used, and any equipment can be sued at room temperature or under reflux heating.

A more specific way of extraction is herein described. Firstly, put an ingredient (green coffee beans) into the processing tank which is filled with extracting solvent, and stir the ingredient. For instance, in the case that the hydroethanol is used as an extracting solvent, the extracting solvent should be used in approx. 5 to 100 times its volume of the ingredient (weight ratio), and the extraction should be done for approx. 30 minutes to 2 hours. After the active substance is eluted into the extracting solvent, the liquid extract is obtained by filtering and reducing the residue. After that, the liquid extract is diluted, concentrated, dried, purified, or processed in the other usual ways, and the inventive dietetic composition can finally be obtained.

Also, the active carbon treatment, the resin absorption treatment, the ion-exchange resin method, the liquid-liquid countercurrent distribution method, or the like can be used as a purification method. However, a large quantity of the dietetic composition is not added to the food or the like. Therefore, unpurified composition can also be used.

According to the research conducted by the inventors, the polar solvent extract of the defatted green coffee beans contains a comparatively large amount of chlorogenic acids and caffeine. Especially the dietetically-functioning chlorogenic acids are concentrated therein. More specifically, the extracts containing chlorogenic acid in concentration of 20 wt % or more, and the extract containing chlorogenic acids (chlorogenic acid, ferulic acid, p-coumaric acid, coffeic acid or the like) in concentration of 45 wt % or more can greatly improve the effect of the dieting method.

The inventive dietetic composition can be used as an ingredient for any food and drink such as, confectionary (chewing gums, candies, caramels, chocolates, cookies, jellies, gummies, tablet shaped sweets or the like), noodles (Japanese buckwheat noodle called Soba, Japanese wheat noodle called Udon, Chinese noodle called Ramen or the like), dairy food (milk, ice cream, yogurt, or the like), seasoning (fermented bean paste called Miso, Soy sauce called Shoyu, or the like), soups, drinks (juice, coffee, black tea, green tea, carbonated drink, or the like).

According to the types of the above foods and drinks, the following ingredients can be added:

Glucose, fructose, sucrose, maltose, sorbitol, stevioside, corn syrup, lactose, citric acid, tartaric acid, malic acid, saccinic acid, lactic acid, L-ascorbic acid, dl-$\alpha$-tocopherol, sodium erythorbate, glycerin, propylene glycol, glycerin fatty acid ester, polyglycerol fatty acid ester, sucrose fatty acid ester, sorbitan fatty acid ester, propylene glycol fatty acid ester, Arabian gum, carrageenan, casein, gelatin, pectine, agar-agar (gelatin made from seaweed), vitamin B family, nicotinic-acid amide, pantothenate acid calcium, amino acids, calcium salts, pigment, aroma chemicals, preservatives, or the like.

A more specific use of the extracting method is herein described. Firstly, spray-dry or freeze-dry the polar solvent extract derived from the defatted green coffee beans with powdered cellulose, then make it powder, granule, tablet, or liquid to easily use with food and drink (ready-to eat meals or the like). Also, it is possible to solve the polar solvent extract derived from the defatted coffee beans into, for instance, oil and fat, ethanol, glycerin, or a mixture of these substances, and to use such a liquid for dry food or drink. Also it is possible to make it into powder or granule by mixing it with a binder such as Arabian gum, dextrin, or the like to add to dry food or drink.

The total amount of the active substance in the inventive dietetic composition which is added to the food and drink is preferably 1 to 20 wt % or less, since the major objective of this invention is disease prevention or health maintenance.

The inventive dietetic composition can be used as the raw material of medicines (including drugs and quasi-drugs). The inventive dietetic composition can be appropriately mixed with raw materials for drug formulations, for instance, vehicles (glucose, sucrose, white soft sugar, sodium chloride, starch, calcium carbonate, kaolin, crystalline cellulose, cacao oil, hydrogenated vegetable oil, talc, or the like), binders (distilled water, normal saline solution, ethanol in water, ethanolic solution, simple syrup, dextrose in water, starch solution, gelatin solution, carboxymethyl cellulose, potassium phosphate, polyvinyl pyrrolidone, or the like), disintegrating agents (alginate sodium, agar-agar, sodium hydrogen carbonate, sodium lauryl sulphate, stearic acid monoglyceride, starch, lactose, powdered aracia, gelatin, ethanol, or the like), suppressive agents for disintegration (white soft sugar, stearin, cacao oil, hydrogenated oil, or the like), absorption promoters (quaternary ammonium base, sodium lauryl sulphate, or the like), adsorbents (glycerin, starch, lactose, kaolin, bentonite, silic acid, or the like), lubricant agents (purified talc, stearate, polyethyleneglycol, or the like)

The inventive dietetic composition can be orally administered in the form of tablets, pills, soft or hard capsules, subtle granules, powders, granules, liquids, or the like. However, it can also be parenterally administered in the form of solution or together with a dispersant, a suspending agent, a stabilizer, or the like by local tissue administration, intradermal injection, subcutaneous injection, intramuscular injection, intravenous injection, or the like. Also, it can be administered in suppository form.

The applied dose can be adjusted according to the method of administration, the condition of the disease, the age of the patient, or the like. However, adults can normally take approx. 0.5 to 5,000 mg of an active substance per day, while children can take 0.5 to 3,000 mg per day.

The compounding ratio of the dietetic composition can be adjusted according to the mode of administration. When the dietetic composition is orally administered or mucosally administered, the applied dose is preferably 0.3 to 15.0 wt %, and when the dietetic composition is parenterally administered, the dose is preferably 0.01 to 10 wt %. The dose varies depending on the conditions. Therefore, the dose which is less than the above-stated amount may be sufficient, or a greater amount may sometimes be needed.

A dietetic composition in this invention contains chlorogenic acid and caffeine. There is a report that a combined formulation of caffeine and some other ingredients gives good results for the slimming therapy (non-patent literature 1). From this result, it can be reasonably expected that the inventive dietetic composition can be used as a drug for external skin use (including cosmetics, drugs, and quasi-drugs) and effectively works in a partial-targeted body slimming program, or to remove cellulite from the body.

The inventive dietetic composition can be mixed with cosmetics such as emulsions, soaps, facial cleansers, bath agents, creams, skin lotions, colognes, shaving creams, shaving lotion, beauty oils, tanning lotions, sunscreen lotions, face powders, foundations, perfumes, facial masks, nail creams, nail enamels, nail-polish removers, eyebrow pencils, blushers, eye creams, eye shadows, mascaras, eye liners, Lip sticks, lip creams, shampoos, hair conditioners, hairdyes, dispersion liquids, cleansing preparations, or the like.

Also, the inventive dietetic composition can be mixed with the drugs and quasi-drugs such as ointments, cream pharmaceuticals, liquids for external use or the like.

Within the functional range of the inventive dietetic composition, the above items for external use can also be mixed with the ingredients of cosmetics, quasi-drugs, or the like. Those ingredients include, for example, oil, higher alcohol, fatty acid, ultraviolet absorber, powder, pigment, surface active agent, polyhydric alcohol and sugar, polymer, biologically active ingredient, solvents, antioxidant, aroma chemical (perfume material), antiseptic. However, those ingredients usable in the present invention are not limited to these examples.

Specific Examples of Oil (Ester-type oil phase ingredient) Triglyceryl 2-ethylhexanoate, cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, isoarachyl neopentanoate, caprylic-capric acid triglyceride, trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprate, propylene glycol di(caprylate/caprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerin oleate, polyglycerin isostearate, dipropyl carbonate, dialkyl carbonate (C12-18), triisocetyl citrate, triisoarachyl citrate, triisooctyl citrate, lauryl lactate, myristyl lactate, cetyl lactate, octyldecyl lactate, triethyl citrate, acetyltriethyl citrate, acet-yltributyl citrate, -trioctyl citrate, diisostearyl malate, 2-ethylhexyl hydroxystearate, 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate and isostearyl 12-stearoylhydroxystearate.

(Hydrocarbon-type oil phase ingredient) Squalane, liquid paraffin, a-olefin oligomer, isoparaffin, ceresin, paraffin, liquid isoparaffin, polybutene, microcrystalline wax and vaseline.

(Animal and plant oil, hardened oil thereof, and wax of natural origin) Animal oils and hardened oils thereof, such as beef tallow, hardened beef tallow, lard, hardened lard, horse oil, hardened horse oil, mink oil, orange roughy oil, fish oil, hardened fish oil and egg yolk oil; plant oils and hardened oils thereof such as avocado oil, almond oil, olive oil, cacao oil, apricot kernel oil, kukui nut oil, sesame oil, wheat germ oil, rice germ oil, rice bran oil, safflower oil, shea butter, soybean oil, evening primrose oil, perilla oil, tea seed oil, tsubaki oil (camellia japonica oil), corn oil, rapeseed oil, hardened rapeseed oil, palm kernel oil, hardened palm kernel oil, palm oil, hardened palm oil, peanut oil, hardened peanut oil, castor oil, hydrogenated castor oil, sunflower oil, grape seed oil, jojoba oil, hardened jojoba oil, macadamia nut oil, meadowfoam seed oil, cottonseed oil, hardened cottonseed oil, conoanut oil, hardened coconut oil; and waxes such as beeswax, high acid number beeswax, lanolin, reduced lanolin, hardened lanolin, liquid lanolin, carnauba wax and montan wax.

(Silicone-type oil phase ingredient) Dimethylpolysiloxane, methylphenylpolysiloxane, methylcyclopolysiloxane, octamethylpolysiloxane, decamethylpolysiloxane, dodecamethylcyclosiloxane, methylhydrogenpolysiloxane, polyether-modified organopolysiloxane, dimethylsiloxanemethylcetyloxysiloxane copolymer, dimethylsiloxanemethylstearoxysiloxane copolymer, alkyl-modified organopolysiloxane, terminal-modified organopolysiloxane, amino-modified silicone oil, amino-modified organopolysiloxane, dimethiconol, silicone gel, acryl silicone, trimethylsiloxysilicic acid and silicone RTV rubber.

(Fluorine-type oil phase ingredient) Perfluoropolyether, fluorine-modified organopolysiloxane, fluorinated pitch, fluorocarbon, fluoroalcohol and fluoroalkyl-polyoxyalkylene-comodified organopolysiloxane.

(2) Specific Examples of Higher Alcohol

Lauryl alcohol, myristyl alcohol, cetyl alcohol, stearyl alcohol, isostearyl alcohol, oleyl alcohol, behenyl alcohol, 2-ethylhexanol, hexadecyl alcohol and octyl dodecanol.

(3) Specific Examples of Fatty Acid

Caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid and 2-ethylhexanoic acid.

(4) Specific Examples of Ultraviolet Absorber

Para-aminobenzoic acid, amyl para-aminobenzoate, ethyldihydroxypropyl para-aminobenzoate, glyceryl para-aminobenzoate, ethyl para-aminobenzoate, octyl para-aminobenzoate, octyldimethyl para-aminobenzoate, ethylene glycol salicylate, octyl salicylate, triethanolamine salicylate, phenyl salicylate, butylphenyl salicylate, benzyl salicylate, homomethyl salicylate, benzyl cinnamate, octyl para-methoxycinnamate, 2-ethylhexyl para-methoxycinnamate, glyceryl mono-2-ethyl hexanoate di para-methoxycinnamate, isopropyl para-methoxycinnamate, diethanolamine para-methoxyhydrocinnamate, diisopropyl diisopropylcinnamic acid ester mixture, urocanic acid, ethyl urocanate, hydroxymethoxybenzophenone, hydroxymethoxybenzophenone sulfonic acid and a salt thereof, dihydroxymethoxybenzophenone, sodium dihydroxymethoxybenzophenone disulfonate, dihydroxybenzophenone, dihydroxydimethoxybenzophenone, hydroxyoctoxybenzophenone, tetrahydroxybenzophenone, butylmethoxydibenzoylmethane, 2,4,6-trianilino-p-(carbo-2-ethylhexyl-1-oxy)-1,3,5-triazine, 2-(2-hydroxy-1-methylphenyl) benzotriazole, methyl-0-aminobenzoate, 2-ethylhexyl-2-cyano-3,3-diphenylacrylate, phenylbenzimidazole sulfuric acid, 3-(4-methylbenzyliden camphor, isopropyldibenzoylmethane, 4-(3,4-dimethoxyphenylmethylene)-2,5-doxy-1-imidazolidinepropionate, and polymer derivatives and silane derivatives thereof.

(5) Specific Examples of Powder and Pigment

Pigments such as Food Red 104, Food Red 201, Food Yellow 4, Food Blue 1 and Food Black 401; lake pigments such as Food Yellow 4 AL lake and Food Yellow 203 BA lake; polymers such as nylon powder, silk powder, urethane powder, Teflon® powder, silicone powder, polymethyl methacrylate powder, cellulose powder, starch, silicone elastomer spherical powder and polyethylene powder; color pigments such as yellow iron oxide, red iron oxide, black iron oxide, chromium oxide, carbon black, ultramarine and iron blue; white pigments such as zinc oxide, titanium oxide and cerium oxide; extender pigments such as talc, mica, sericite, kaolin and plate barium sulfate; pearl pigments such as mica titanium; metal salts such as barium sulfate, calcium carbonate, magnesium carbonate, aluminum silicate and magnesium silicate; inorganic powders such as silica and alumina; metal soaps such as aluminum stearate, magnesium stearate, zinc palmitate, zinc myristate, magnesium myristate, zinc laurate and zinc undecylenate; bentonite; smectite; and boron nitride.

The shape (e.g., sphere, bar, needle, plate, amorphous, scale, spindle) and the particle size of these powders are not particularly limited.

These powders may or may not be previously surface-treated by a conventionally known surface treatment such as fluorine compound treatment, silicone treatment, silicone resin treatment, pendant treatment, saline coupling agent treatment, titanium coupling agent treatment, lubricant treatment, N-acylated lysine treatment, polyacrylic acid treatment, metal soap treatment, amino acid treatment, lecithin treatment, inorganic compound treatment, plasma treatment and mechanochemical treatment.

(6) Specific Examples of Surfactant

Anionic surfactant: Fatty acid soap, a-acyl sulfonate, alkyl sulfonate, alkylallyl sulfonate, alkylnaphthalene sulfonate, alkyl sulfate, POE alkyl ether sulfate, alkylamide sulfate, alkyl phosphate, POE alkyl phosphate, alkylamide phosphate, alkyloylalkyl taurine salt, N-acylamino acid salt, POE alkyl ether carbonate, alkyl sulfosuccinate, sodium alkylsulfoacetate, acylated hydrolyzed collagen peptide salt and perfluoroalkylphosphoric acid ester.

Cationic surfactant: Alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, behenic acid amidopropyldimethyl hydroxypropylammonium chloride, diethylaminoethylamide stearate, dimethylaminoethylamide stearate, dimethylaminopropylamide stearate and lanolin derivative quaternary ammonium salt.

(Amphoteric surfactant) Carboxybetaine type, amidobetaine type, sulfobetaine type, hydroxysulfobetaine type, amidosulfobetaine type, phosphobetaine type, aminocarboxylate type, imidazoline derivative type and amidoamine type.

(Nonionic surfactant) Propylene glycol fatty acid ester, glycerin fatty acid ester, polyglycerin fatty acid ester, sorbitan fatty acid ester, POE sorbitan fatty acid ester, POE sorbitol fatty acid ester, POE glycerin fatty acid ester, POE alkyl ether, POE fatty acid ester, POE hydrogenated castor oil, POE castor oil, POE-POP copolymer, POE-POP alkyl ether, polyether-modified silicone lauric acid alkanolamide, alkylamine oxide and hydrogenated soybean phospholipid.

(Natural-type surfactant) Lecithin, saponin and sugar-type surfactant.

(7) Specific Examples of Polyhydric Alcohol and Sugar

Ethylene glycol, diethylene glycol, polyethylene glycol, propylene glycol, dipropylene glycol, polypropylene glycol, glycerin, diglycerin, polyglycerin, 3-methyl-1,3-butanediol, 1,3-butylene glycol, sorbitol, mannitol, raffinose, erythritol, glucose, sucrose, fruit sugar, xylitol, lactose, maltose, maltitol, trehalose, alkylated trehalose, mixed isomerized sugar, sulfated trehalose and pullulan. Chemically modified products thereof can also be used.

(8) Specific Examples of Polymer Compound

Anionic polymer compounds such as acrylic acid ester/methacrylic acid ester copolymer (PLUS-SIZE, produced by Sogokagaku K. K.), vinyl acetate/crotonic acid copolymer (Resin 28-1310, produced by NSC), vinyl acetate/crotonic acid/vinyl neodecanate copolymer (28-2930, produced by NSC), methyl vinyl ether maleic acid half ester (GANTREZ ES, produced by ISP), T-butyl acrylate/ethyl acrylate/methacrylic acid copolymer (RUBIMER, produced by BASF), vinylpyrrolidone/vinyl acetate/vinyl propionate copolymer (RUBISCOL VAP, produced by BASF), vinyl acetate/crotonic acid copolymer (RUBISET CA, produced by BASF), vinyl acetate/crotonic acid/vinylpyrrolidone copolymer (RUBISET CAP, produced by BASF), vinylpyrrolidone/acrylate copolymer (RUBIFLEX, produced by BASF), acrylate/acrylamide copolymer (ULTRAHOLD, produced by BASF), vinyl acetate/butyl maleate-isobornyl acrylate copolymer (ADVANTAGE, produced by ISP), carboxy vinyl polymer (CARBOPOL, produced by BF Goodrich) and acrylic acid-alkyl methacrylate copolymer (PAMUREN, produced by BF Goodrich); amphoteric polymer compounds such as acetic acid amphoteric compound of dialkylaminoethyl methacrylate polymer (YUKAFORMER, produced by Mitsubishi Chemical) and octylacrylamide acrylate/hydroxypropyl acrylate/butylaminoethyl methacrylate copolymer (AMPHOMER, produced by NSC); cationic polymer compounds such as quaternized compound of vinylpyrrolidone/dimethylaminoethyl methacrylate (GAFQUAT, produced by ISP) and methyl vinyl imidazolium chloride/vinylpyrrolidone copolymer (RUBICOTE, produced by BASF); and nonionic polymer compounds such as polyvinylpyrrolidone/vinyl acetate copolymer (RUBISCOL VA, produced by BASF) and vinylpyrrolidone/dimethylaminoethyl methacrylate copolymer (COPOLYMER VC713, produced by ISP).

In addition, polymer compounds of natural origin, such as cellulose and derivatives thereof, calcium alginate, pullulan, agar, gelatin, tamarind seed polysaccharides, xanthane gum, carrageenan, high-methoxyl pectin, low-methoxyl pectin, guar gum, gum arabi, crystal cellulose, arabino galactan, karaya gum, tragacanth gum, alginic acid, albumin, casein, cardrun, gellan gum and dextran, can also be suitably used.

(9) Specific Examples of Biologically Active Ingredient

The biologically active ingredient may include substances which are capable of imparting some biological activity to skin, when such a substance is applied to the skin. Specific examples thereof may include: whitening ingredient, anti-inflammatory, age resistor, ultraviolet protection, slimming agent, skin tightening agent, antioxidant, hair restorer, hair growing agent, moisturizer, blood circulation accelerator, antibacterial agent, bactericide, desiccant, cooling agent, warming agent, vitamin compound, amino acid, wound healing accelerator, torpent, analgetic, cell activator and enzyme ingredient.

Suitable examples of the ingredient to be blended therefor may include: angelica extract, avocado extract, hydrangea extract, althea extract, arnica extract, aloe extract, apricot extract, apricot core extract, ginkgo extract, fennel extract, turmeric extract, oolong tea extract, rose fruit extract, echinacea leaf extract, scutellaria root extract, phellodendron bark extract, goldthread extract, barley extract, hypericum extract, white nettle extract, watercress extract, orange extract, sea salt, seaweed extract, hydrolyzed elastin, hydrolyzed wheat powder, hydrolyzed silk, chamomile extract, carrot extract, artemisia capillaris extract, glycyrrhiza extract, sabdariffa extract, pyracantha fortuneana fruit extract, kiwi extract, cinchona extract, cucumber extract, guanosine, gardenia extract, sasa albo-marginata extract, sophora root extract, walnut extract, grapefruit extract, clematis extract, chlorella extract, mulberry bark extract, gentian extract, black tea extract, yeast extract, burdock extract, fermented rice bran extract, rice germ oil, comfrey extract, collagen, cowberry extract, asiasarum root extract, bupleurum falcatum root extract, umbilical cord extract, salvia extract, saponaria extract, bamboo grass extract, crataegus extract, zanthoxylum fruit extract, shiitake mushroom extract, rehmannia root extract, lithospermum root extract, perilla extract, linden extract, filipendula extract, peony root extract, calamus rhizome extract, birch extract, horsetail extract, ivy extract, hawthorn extract, sambucus nigra extract, yarrow extract, peppermint extract, sage extract, mallow extract, cnidium rhizome extract, swertia herb extract, soy extract, jujube extract, wild thyme extract, green tea extract, clove extract, cogon extract, citrus unshiu peel extract, angelica root extract, calendula extract, peach seed extract, bitter orange extract, houttuynia extract, tomato extract, natto extract, ginseng extract, garlic extract, wild rose extract, hibiscus sabdariffa flower extract, ophiopogon tuber extract, parsley extract, honey, witch hazel extract, pellitory extract, isodonis extract, matricaria extract, loquat extract, coltsfoot extract, butterbur scape extract, Poria cocos extract, butcher bloom extract, grape extract, propolis, luffa extract, safflower extract, peppermint extract, linden extract, peony extract, hop extract, pine extract, horse chestnut extract, skunk cabbage extract, sapindaceae extract, balm mint extract, peach extract, cornflower extract, eucalyptus extract, saxifrage extract, citrus extract, coix seed extract, mugwort extract, lavender extract, apple extract, lettuce extract, lemon extract, Chinese milk vetch extract, rose extract, rosemary extract, Roman chamomile extract and royal jelly extract.

Other examples may include biopolymers such as deoxyribonucleic acid, mucopolysaccharide, sodium hyaluronate, sodium chondroitin sulfate, collagen, elastin, chitin, chitosan and hydrolyzed eggshell membrane; moisture retentive ingredients such as amino acid, hydrolyzed peptide, sodium lactate, urea, sodium pyrrolidonecarboxylate, betaine, whey and trimethylglycine; oily ingredients such as sphingolipid, ceramide, phytosphingosine, cholesterol, cholesterol derivatives and phospholipid; anti-inflammatory such as E-aminocaproic acid, glycyrrhizic acid, -glycyrrhetic acid, lysozyme chloride, guaiazlene and hydrocortisone; vitamins such as vitamin A, vitamin B2, vitamin B6, vitamin D, vitamin E, calcium pantothenate, biotin and nicotinic acid amide; active ingredients such as allantoin, diisopropylamine dichloroacetate and 4-aminomethylcyclohexanecarboxylic acid; antioxidants such as tocopherol, carotenoid, flavonoid, tannin, lignin and saponin; cell activators such as a-hydroxy acid and hydroxy acid; blood circulation accelerators such as y-orizanol and vitamin E derivatives; wound healing agents such as retinol and retinol derivatives; whitening agents such as albumin, kojic acid, placenta extract, sulfur, ellagic acid, linoleic acid, tranexamic acid and glutathione; and hair growing agents such as cepharanthine, glycyrrhiza extract, capsicum tincture, hinokitiol, iodized garlic extract, pyridoxine hydrochloride, DL-a-tocopherol, DL-a-tocopheryl acetate, nicotinic acid, nicotinic acid derivatives, calcium pantothenate, D-pantothenyl alcohol, acetyl pantothenylethyl ether, biotin, allantoin, isopropylmethylphenol, estradiol, ethynyl estradiol, capronium chloride, benzalkonium chloride, diphenhydramine hydrochloride, Takanal, camphor, salicylic acid, vanillylamide nonylate, vanillylamide nonanoate, pyroctone olamine, glyceryl pentadecanoate, L-menthol, mononitroguaiacol, resorcinol, y-aminobutyric acid, benzethonium chloride, mexiletine hydrochloride, auxin, female hormone, cantharis tincture, cyclosporine, zinc pyrithione, hydrocortisone, minoxidil, polyoxyethylene sorbitan monostearate, peppermint oil and SADANISHIKI extract.

(10) Specific examples of antioxidant Sodium hydrogensulfite, sodium sulfite, erythorbic acid, sodium erythorbate, dilauryl thiodipropionate, tocopherol, tolylbiguanide, nordihydroguaiaretic acid, parahydroxy anisole, butylhydroxy anisole, dibutylhydroxy toluene, ascorbyl stearate, ascorbyl palmitate, octyl gallate, propyl gallate, carotenoid, flavonoid, tannin, lignin, saponin and plant extracts having antioxidant effect, such as apple extract and clove extract.

(11) Specific examples of solvent Purified water, ethanol, lower alcohol, ethers, LPG, fluorocarbon, N-methylpyrrolidone, fluoroalcohol, volatile linear silicone and next generation fleon (such as fluorocarbon, chlorofluorocarbon, CFC).

EXAMPLES

The examples in this invention are herein described. The descriptions indicated below are only the explanations to determine the diet effect or the like on the inventive dietetic composition. They are not limited to the products and method for manufacturing the products.

(Method for Manufacturing the Dietetic Composition)

Indonesia's robusta green coffee beans are used as an ingredient. Firstly, compress the green coffee beans to reduce the oil, then obtain one kilogram of the compressed coffee beans. Secondly, crush all the compressed coffee beans, reflux them with hexane, and remove the remaining oil from them. Thirdly, extract the defatted coffee beans with the hydroethanol having the ethanol concentration of 60 wt % and dry the ethanol extract so that 60 grams of the green coffee bean extract (example: dietetic composition) can be obtained. Also, HPLC (high-performance liquid chromatography) of the ingredient of the green coffee bean extract detected approx. 45 wt % of chlorogenic acids (including approx. 20 wt % of chlorogenic acid) and approx. 10 wt % of caffeine.

(Verification Test (In Vivo) for Diet Effect on Weight Gain and Body Fat Accumulation)

Also let the mice eat freely three types of foods mixed with the green coffee bean extract, caffeine, or chlorogenic acid respectively (each ingredient should be put until the prescribed content ratio is obtained) so as to verify each diet effect on the weight gain and body fat accumulation.

Let the mice (ddY, male, 6-week-old) eat freely the three types of foods (CE-2, CLEA Japan, Inc.) mixed with the green coffee bean extract (0.5 wt % and 1.0 wt %), caffeine (0.05 wt % and 0.1 wt %), or chlorogenic acid (0.15 wt % and 0.3 wt %) respectively for 13 days. The weight of each mouse was measured every other day during the feeding period, and the weight of the epididymal fat of each mouse on the last day of the feeding period. There was little difference in intake of the food among the control group (for only normal food given) and individual sample administration groups. The results are shown in FIGS. 1 and 2.

As shown in FIG. 1, it is obvious that the green coffee bean extract (Example) has a suppressive effect on the weight gain. However the chlorogenic acid and caffeine contained in the green coffee bean extract do not have a sufficient suppressive effect on the weight gain. From this result, it is considered that specific substances other than the chlorogenic acid and caffeine contained in the green coffee bean extract (Example) are complexly associated with the suppressive factors of the weight gain.

Figure 2:
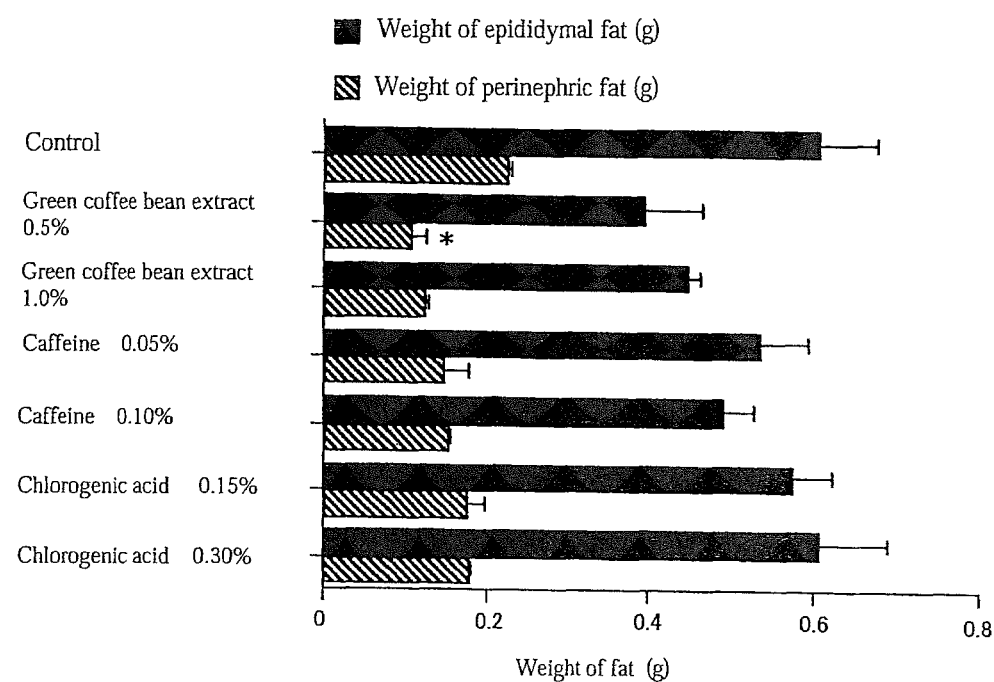
FIG. 2 is a graph showing an effect on the visceral fat of mice which continuously take an extract derived from the green coffee beans and substances derived from coffee beans (caffeine and chrologenic acid).

Also, as shown in FIG. 2, the green coffee bean extract (Example) indicates a suppressive effect on the accumulation of the weight of the epididymal fat and the weight of perinephric fat. Chlorogenic acid and caffeine slightly indicates a suppressive effect on the accumulation of the fat.

Figure 3:
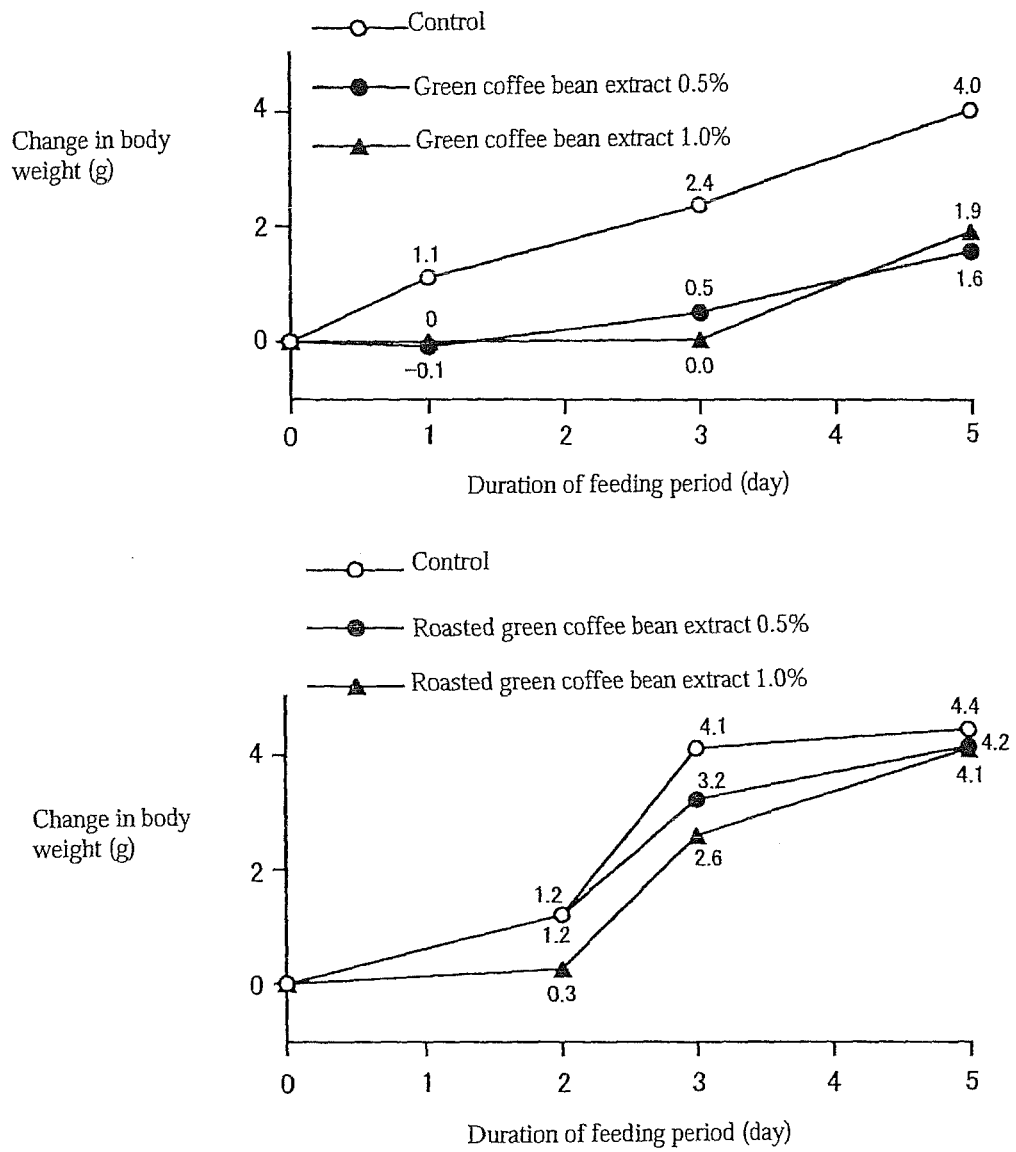
FIG. 3 is a graph showing an effect on the weight gain of mice which continuously take an extract derived from the green coffee beans and roasted coffee beans.

FIG. 3 shows a comparison of the anti-obesity effect on the weight gain of the mice which ate different foods with the green coffee bean extract (Example) or with the roasted coffee bean extract (Comparative example). In the test, the non-defatted green coffee beans are roasted and extracted under the same condition to obtain the green coffee bean extract (Example). Also, the weight change of the mice when using the roasted coffee bean extract should be measured for 5 days under the same condition as the mice using the aforementioned green coffee bean extract (Example).

As shown in FIG. 3, the green coffee bean extract (Example) has a greater suppressive effect on the weight gain of the mice compared to that of the roasted coffee bean extract (Comparative example). Therefore, the green coffee bean extract (Example) has obviously a greater diet effect compared to that of the roasted coffee bean extract.

Next, the diet effect of the dietetic composition on the weight gain, which is made by the green coffee bean extract (Example) and the existing dietetic materials (*salacia* extract, evening primrose extract, sesamine, *garcinia*), can be verified in the following Chart 1. *Salacia* extract can be obtained by extracting the *salacia* root with solvent. Evening primrose extract can also be obtained by extracting the evening primrose with solvent.

As a test method, as shown in Chart 1, a four-day experiment was conducted with the mice (ddY, male, 5-week-old) to freely eat the food (CE-2, CLEA Japan, Inc.) mixed with the sample as indicated in Chart 1. The weight of each mouse was measured on the first day and on the final day of the experimental period.

In the test, green coffee bean extract (0.5 wt %), *salacia* extract (0.5 wt %), evening primrose extract (3.0 wy %), sesamine (0.5 wy %) and *garcinia* (1.0 wy %) should be respectively mixed with the food.

CHART 1

| Class | Weight (g) | | Weight increase (g) | Difference in the weight compared to the control (g) |
| --- | --- | --- | --- | --- |
| | Prior to the test | 4<sup>th</sup> day | | |
| Control | 26.85 ± 1.02 | 31.23 ± 1.18 | 4.38 | — |
| Green coffee bean extract | 26.71 ± 0.74 | 30.47 ± 0.94 | 3.76 | −0.62 |
| Green coffee bean extract & salacia extract | 27.20 ± 1.13 | 31.42 ± 0.54 | 3.06 | −1.32 |
| Salacia extract | 27.29 ± 1.29 | 30.64 ± 1.85 | 3.35 | −1.03 |
| Green coffee bean extract & evening primrose extract | 28.26 ± 0.86 | 31.45 ± 1.443 | 3.20 | −1.18 |
| Evening primrose extract | 28.18 ± 1.24 | 1.58 ± 1.10 | 3.39 | −0.99 |
| Green coffee bean extract & sesamine | 27.30 ± 0.89 | 30.76 ± 1.64 | 3.45 | −0.93 |
| Sesamine | 27.36 ± 0.86 | 30.91 ± 1.79 | 3.55 | −0.83 |
| Green coffee bean extract & garcinia | 27.47 ± 0.88 | 30.55 ± 1.41 | 3.08 | −1.3 |
| Garcinia | 26.93 ± 1.24 | 30.51 ± 1.96 | 3.58 | −0.8 |

Average ± standard error (n = 5)

As shown in Chart 1, when using the green coffee bean extract (Example) together with the *salacia* extract, evening primrose extract, sesamine, or *garcinia*, the suppressive effect of those complex ingredients on the weight gain greatly increases, compared with the administration of the green coffee bean extract alone.

Thus, in the diet prescription of the green coffee bean extract (Example), the combination of the green coffee bean extract (Example) with the *salacia* extract, evening primrose extract, sesamine, or *garcinia* can increase the diet effect. In other words, the diet of the green coffee bean extract (Example) combined with one or more substances from among the *salacia* extract, evening primrose extract, sesamine, or *garcinia* can produce a greater effect.

In other examples, the green coffee bean extract combined with one or more substances from among *gymnema sylvestre*, mulberry leaf, guava leaf, white kidney bean, glucomannan, yacon, chia seed, fenugreek, wheat amylase inhibitor, balsam pear, conjugated linoleic acid, L-carnitine, *coleus forskohlli*, yerba mate, *astibe thunbergii, citrus aurantium*, paprika, capsiate, *cassia polyphenol, malus* extract, green tea extract, green tea polyphenol, soybean isoflavone, purple rice extract, chitosan, raspberry ketone, or the like also show an excellent effect on the diet.

(Verification Test of the Diet Effect on the Fat Metabolic Pathway)

(1) Verification Test of the Suppressive Effect on the Absorption of Fat.

a. Retarding Effect on Fat Absorption (In Vivo):

Administer a single dose of olive oil to the mice. Then verify the effect of the green coffee bean extract (Example) on the absorption of fat in the body of each mouse.

In the test, blood samples were taken from 20-hour fasting mice (ddY, male, 6-week-old). Half an hour after the blood sampling, the gum aracia suspension (10 mL/kg) with the green coffee bean extract (Example) in concentration of 5 w/v % was orally administered to the mice. One hour later, the olive oil was orally administered to the mice. Two, four, and six hours later, the blood samples were respectively taken. Then, the blood serum was separated from the blood sample and the concentration of triglyceride was measured by using the enzyme method (triglyceride E-Test Wako, Wako Pure Chemical Industries Ltd. of Japan).

Figure 4:
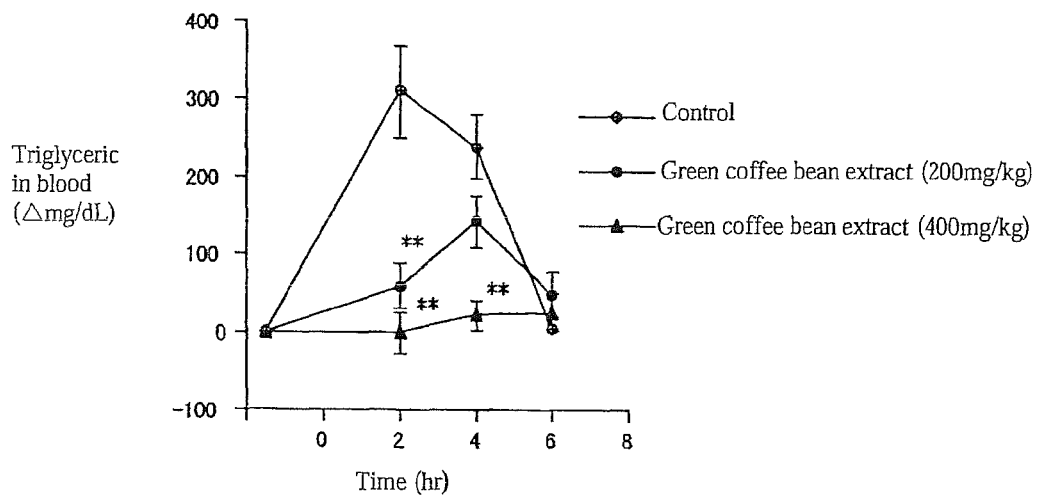
FIG. 4 is a graph showing an effect of the extract derived from the green coffee beans on the triglyceride in the blood when olive oil is taken into the body.

As shown in FIG. 4, compared to the control group, the green coffee bean extract (Example) shows a significant suppressive effect on the blood triglyceride level.

Therefore, it is considered that the green coffee bean extract has a strong suppressive effect on the absorption of fat.

b. Pancreatic Lipase Inhibitory Activity (In Vitro):

In regard to the green coffee bean extract (Example) and its contained substances (caffeine and chlorogenic acid), the pancreatic lipase inhibitory activity related to the lipolysis was evaluated by in vitro experiment.

Figure 5:
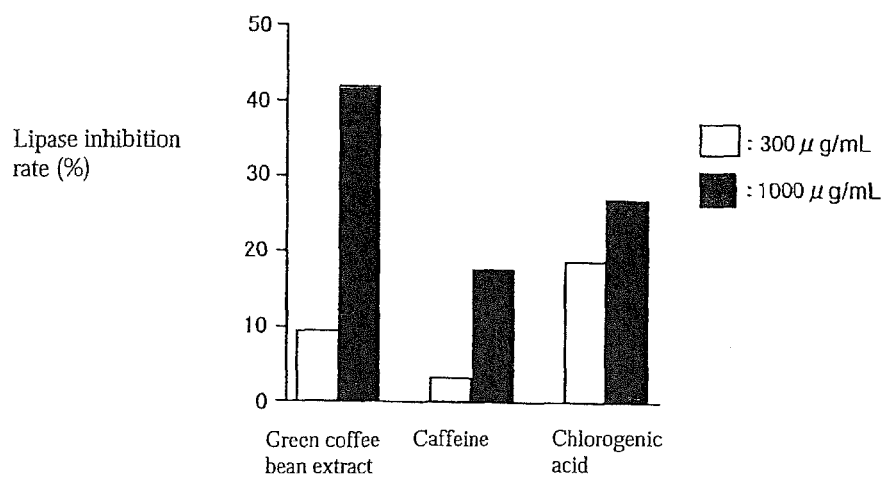
FIG. 5 is a graph showing the pancreatic lipase inhibitory activity of the extract derived from the green coffee beans and substances derived from coffee beans (caffeine and chlorogenic acid).

The lipase inhibitory activity was analyzed by using a pancreatic lipase (product of SIGMA ADLRICH JAPAN K.K, final concentration 105.8 units/mL) derived from the swine and a lipase kit-s (Dainippon Pharmaceutical Co., Ltd.). FIG. 5 shows the result.

As shown in FIG. 5, the green coffee bean extract (Example), the chlorogenic acid and the caffeine indicate a pancreatic lipase inhibitory activity and all three substances suppress the fat absorption level. Yet, the green coffee bean extract shows a greater effect on the pancreatic lipase inhibitory activity than that of chlorogenic acid and caffeine. Considering the content of the chlorogenic acid (approx. 20 wt %) and caffeine (approx. 10 wt %) in the green coffee bean extract, it is thought that substances other than the chlorogenic acid and caffeine affect the pancreatic lipase inhibitory activity.

(2) Verification Test of Inhibitory Effect on Fat Accumulation a. Suppressive Effect on 3T30L1 Adipocyte Degradation (In Vitro):

Apply the green coffee bean extract (Example) and its contained substance (caffeine and chlorogenic acid) to the mouse adipose cell line (3T30L1) in culture and verify the effect on the fat accumulation after the differentiation induction.

The test method is herein described. Cultivate the 3T30L1 adipose cell (5×10$^4$ cells/mL) in DMEM medium (high glucose) including fetal calf serum (10 wt %) for two days. Then, replace the medium with a different type of medium containing insulin (1ag/mL), dexamethasone (0.25 µM) and isobutyl methyl xanthin (0.5 mM) for the differentiation induction. Two days later, replace the medium again with the different medium containing the samples and insulin (1 µg/mL), and cultivate them for six days replacing the medium every other day. After completing the cultivation, analyze the glycerol 3-phosphate dehydrogenase (GPDH) activity which is to be an indicator of the concentration of triglyceride in the cell and adipocyte differentiation.

Figure 6:
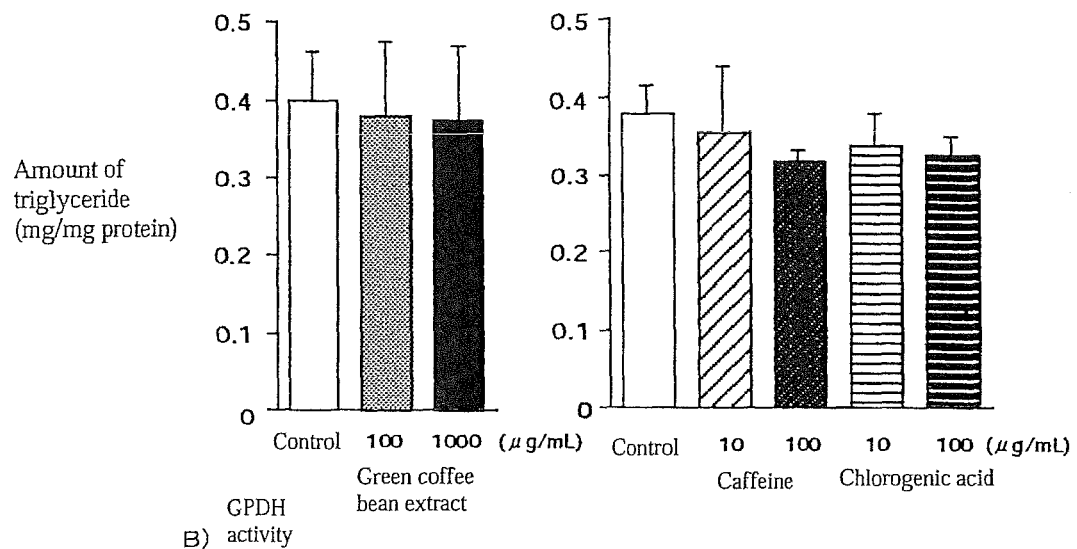
FIG. 6 is a graph showing the effect on a 3T3-L1 adipocyte differentiation of the extract derived from the green coffee beans and substances derived from coffee beans (caffeine and chlorogenic acid).
Figure 6:
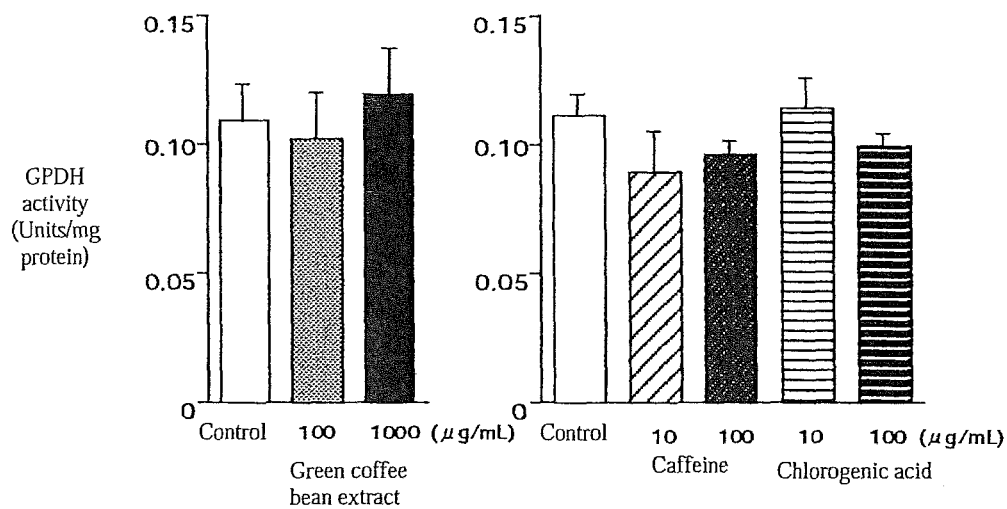

As shown in FIG. 6, the green coffee bean extract (Example), the caffeine, and the chlorogenic acid indicate a mild inhibitory effect on the fat accumulation (decrease in triglyceride accumulation).

Also, it is obvious that the green coffee bean extract (Example), the caffeine, and the chlorogenic acid have a mild inhibitory effect on the GPDH activity which is to be an indicator of the concentration of triglyceride in the cell and adipocyte differentiation. Furthermore, the concentration indicates no toxicity.

b. Suppressive Effect on Fatty Liver (In Vivo):

The effect on the hepatic lipid (triglyceride and total cholesterol) is evaluated after the green coffee bean extract and its contained substances (caffeine, and chlorogenic acid) are continuously administered to the mice for two weeks.

The test method is herein described. Keep the mice (ddY, male, 5-week-old) in the laboratory for one week. Then, divide them into four groups and orally administer the samples suspended in the gum aracia (5 w/v %) once a day for two weeks. On the final day of the test, remove the livers from the non-food-derived mice, and measure the amount of liver triglyceride and total cholesterol contained therein by using the test kit of Wako Pure Chemical Industries Ltd. of Japan. (The result shown in FIG. 7)

Figure 7:
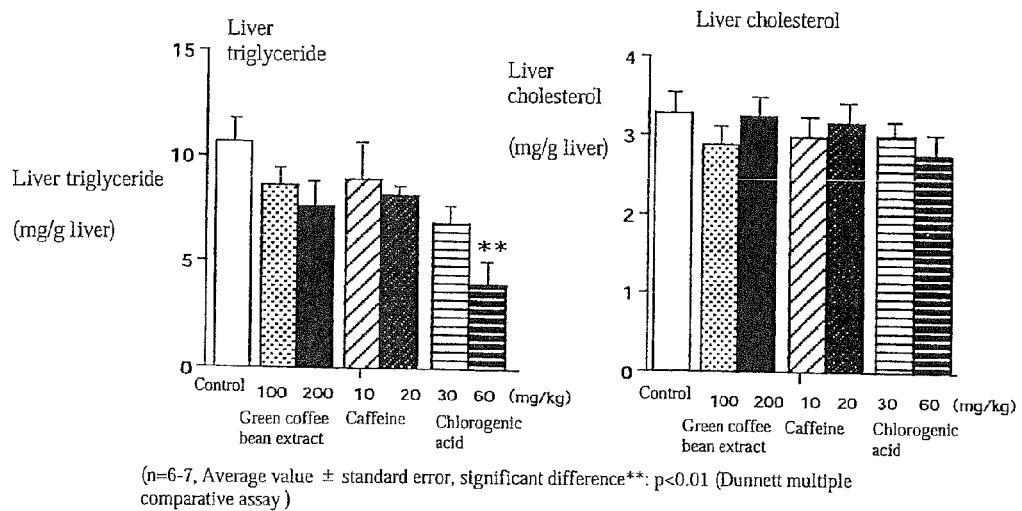
FIG. 7 is a graph showing the effect on the hepatic fatty of the mice which continuously takes the extract derived from the green coffee beans and substances derived from coffee beans (caffeine and chlorogenic acid).

As shown in FIG. 7, the green coffee bean extract (Example), the caffeine and the chlorogenic acid reduce the liver triglyceride. The caffeine and the chlorogenic acid especially indicate a strong effect. On the other hand, the total cholesterol value is almost the same as the value of the control group. As the results of this test show, it is thought that the green coffee bean extract has a suppressive effect on the accumulation of neutral fat in the liver and that the caffeine and chlorogenic acid are related with the suppressive effect.

(3) Verification Test of Promotive Effect on Lipolysis a. Lipolysis Effect (In Vitro):

It is known that caffeine enhances the activity of lipase in the adipose cell and promotes the degradation of neutral fat. In this test, the lipolysis effect of the green coffee bean extract and its contained substances (caffeine and chlorogenic acid) are respectively reviewed, compared to the existing dietetic composition.

The test method is herein described. Remove the epididymal fat from male Wister rats, and incubate the fat in each sample solved in Medium 199 (medium culture) at a temperature of 37° C. for three hours. After completing the incubation, remove the fat and measure the amount of glycerol in the medium by using F-kit glycerol (product of Nippon Roche). The result is shown in FIG. 8.

Figure 8:
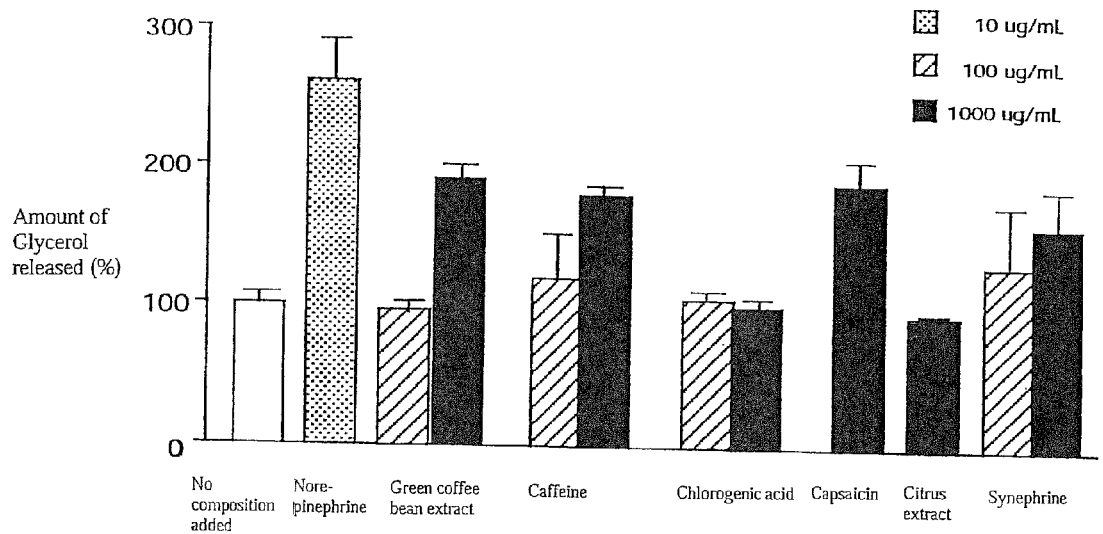
FIG. 8 is a graph showing the effect of the extract derived from the green coffee beans, substances derived from coffee beans (caffeine and chlorogenic acid) and lipolytic substances on the glycerol release of the epididymal fat.

As shown in FIG. 8, when using 1000 µg/mL of the green coffee bean extract (Example), the lipolysis effect is the same as that of the single compound—caffeine, capsaicin, and synephrine, and is greater than that of the citrus extract containing approx. 30 wt % of synephrine. Also, the chlorogenic acid indicates a mild lipolysis effect.

b. Hypotriglyceridemic Action in Blood (In Vivo)

The green coffee bean extract or its contained substances (caffeine and chlorogenic acid) are respectively administered to the food-deprived mice. Then the effects on the blood triglyceride level are observed.

The test method is herein described. First of all, take a blood sample from the veins of the 24-hour food-deprived mice (ddy. Male, 6-week-old). Half an hour later, orally apply each sample (10 mL./kg) suspended with the gum aracia of 5 w/v % to the mice. Then, take a blood sample from the mice every one hour, and measure the blood triglyceride levels. Under the same condition, measure the blood triglyceride levels of the mice as a control, in which only gum aracia is orally administered.

Figure 9:
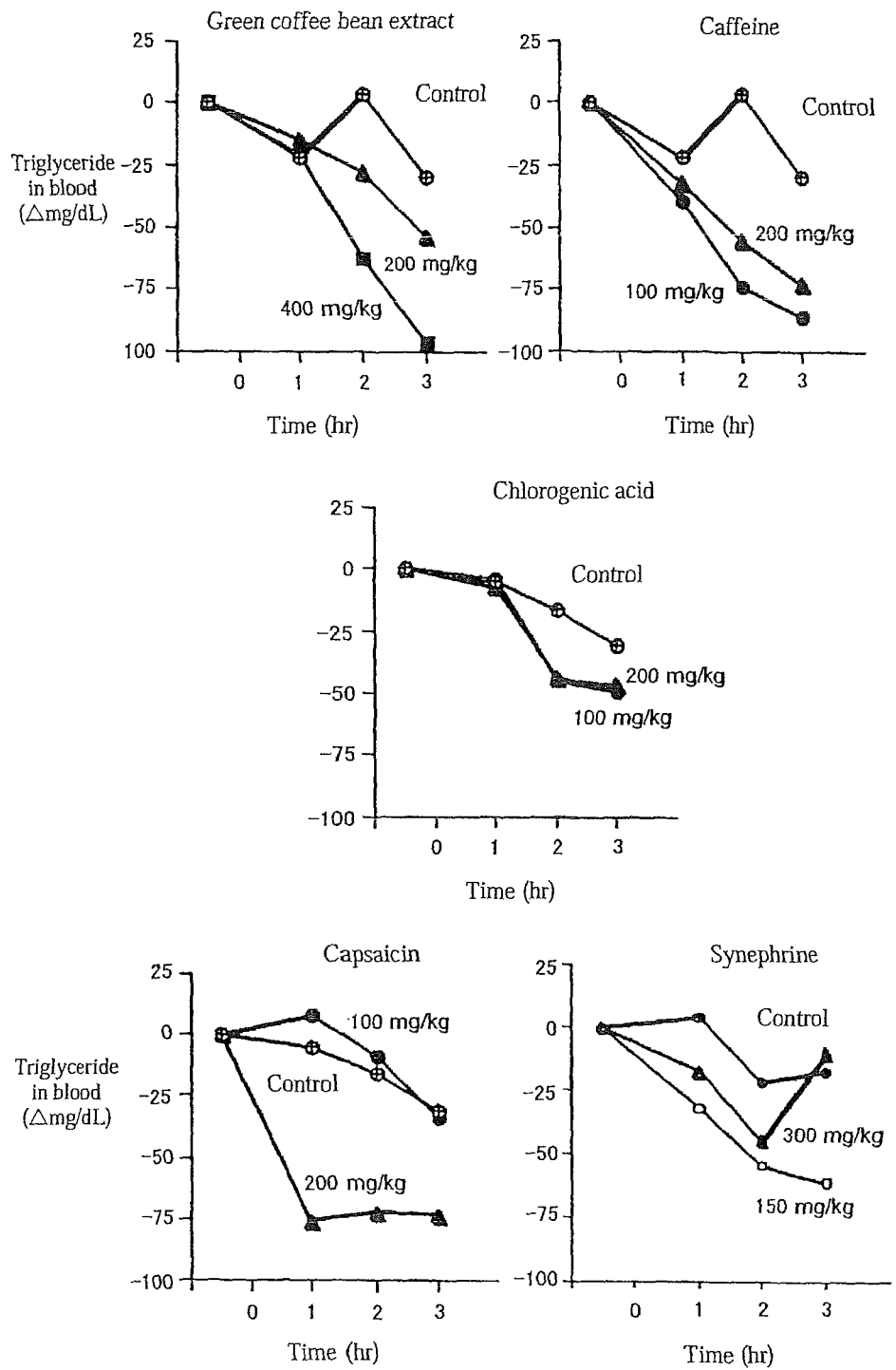
FIG. 9 is a graph showing the effect of the extract derived from the green coffee beans, substances derived from coffee beans (caffeine and chlorogenic acid) and the existing dietetic materials on the triglyceride in the blood of the mice.

As shown in FIG. 9, the green coffee bean extract (Example) indicates a strong lowering effect on the blood-triglyceride, which is similar to the effect of capsaicin. Also, the caffeine indicates a strong lowering effect on the blood-triglyceride. On the other hand, the chlorogenic acid indicates a lowering effect on the blood-triglyceride identical to the effect of synephrine.

Considering the above test result, it is thought that the green coffee bean extract (Example) has a promotive effect on the lipolysis of the adipose cell, and that the caffeine and chlorogenic acid are related to this effect.

(4) Verification Test of the Promotive Effect on Fat-Burning Activity.

(Verification Test of the Promotive Effect on Carnitine Palmitoyltransferase (CPT) Activity: In Vivo).

The food mixed with the green coffee bean extract (Example) was given to the mice, and the carnitine palmitoyltransferase (CPT) activity which contributes the β-oxidation of the fat-burning metabolism is measured.

The test method is herein described. Firstly, let the mice (ddY, male, 7-week-old) eat freely for six days the food (CE-2, product of CLEA Japan, Inc) which is mixed with the green coffee bean extract (0.5 and 1 wt %). Secondly, after dislocating the cervical spines, remove the livers from the mice, and add the buffer solution (pH7.4) containing 0.25M of sucrose and 1.0 mM of EDTA which are in six times its volume of the liver for homogenate and centrifugal separation (3,000 r.p. 10 min.). Thirdly, centrifugalize the supernatant (11,000 r.p. 10 min.) to obtain precipitate (mitochondrial fraction), and suspend it with the buffer solution (2.5 mL). After protein determination, measure the CPT activity by the DTNB method. The result is indicated in FIG. 10.

Figure 10:
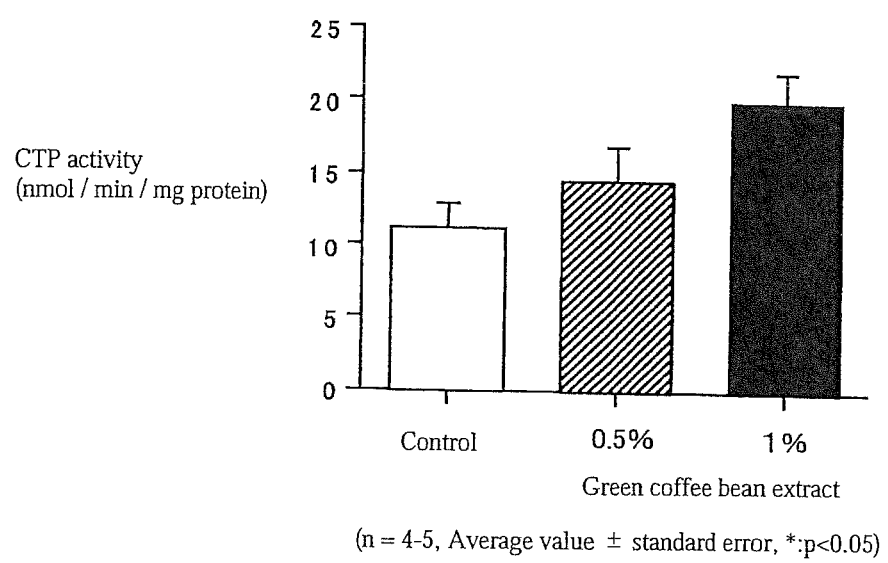
FIG. 10 is a graph showing the effect of the extract derived from the green coffee beans on promoting activity of the hepatic mitochondrial fraction CPT.
Figure 11:
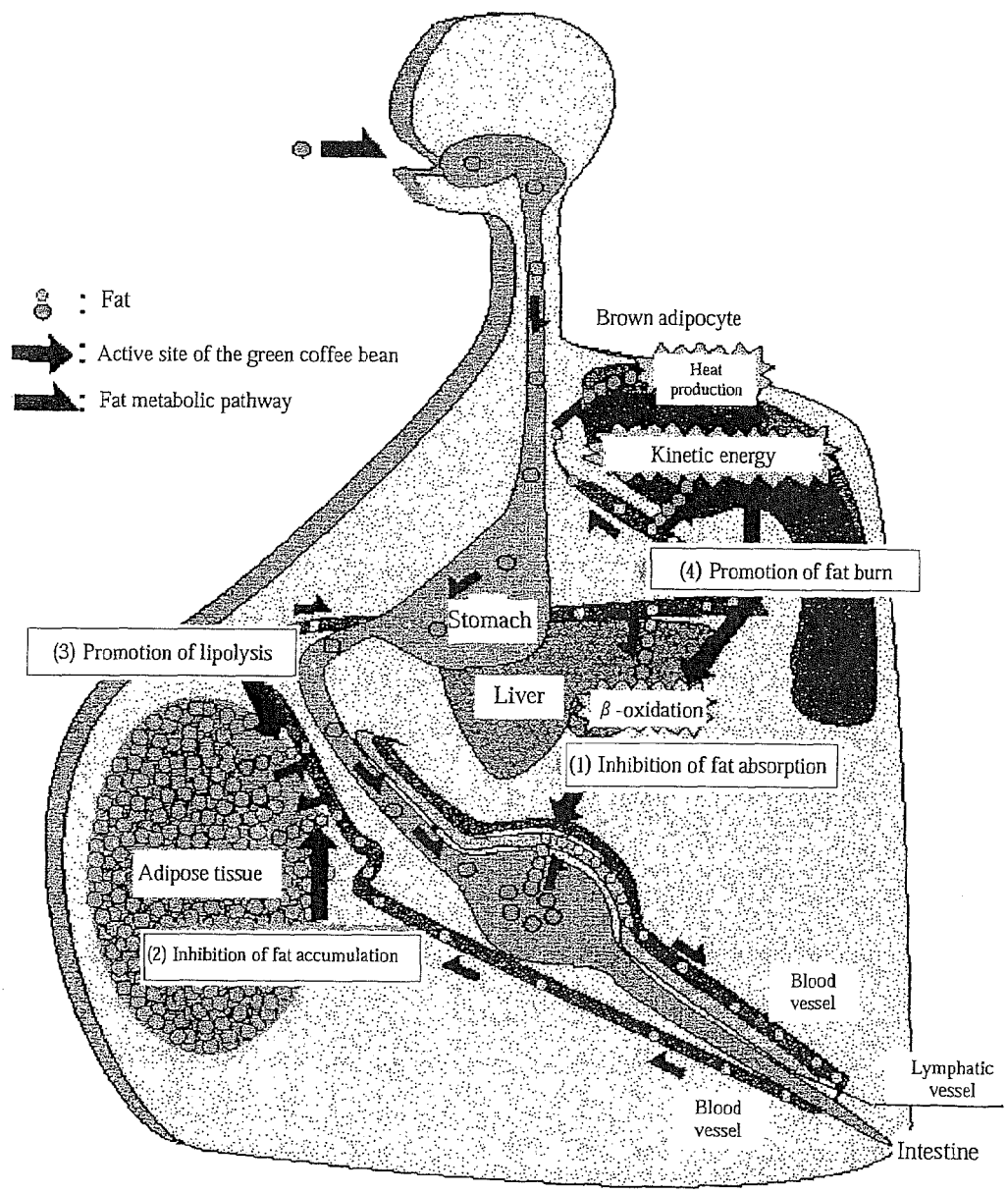
FIG. 11 is an illustration indicating the diet effect in the fat metabolic pathway.

As shown in FIG. 10, the green coffee bean extract (Example) indicates a dose-dependent promotive effect on the CPT activity. Thus, it is thought that the green coffee bean extract (Example) promotes the CPT activity and supports the fat-burning activity.

(Verification Test of the Effect on Diabetes Prevention)

a. Retarding Effect on Carbohydrate Absorption (In Vivo):

Carbohydrate is administered to the mice. Then the suppressive effect of the green coffee bean extract on the elevation of the blood glucose levels is verified by using the mouse carbohydrate load model.

The test method is herein described. First of all, take the blood sample from the 18-hour food-deprived mice (ddy, male, 6-week-old). Immediately after the blood sampling, orally administer the green coffee bean extract (Example) aqueous solution (10 mL/kg) to the mice. One hour later, orally administer a dose (5 mL/kg) of the glucose (0.5 g/kg) or sucrose (2 g/kg) to the mice. Then, take the blood samples a half an hour, one hour, and two hours later. Furthermore, separate the serum from the blood and determine the glucose concentration by the enzyme method (determiner GL-E: product of Kyowa Medex Co., Ltd).

Figure 12:
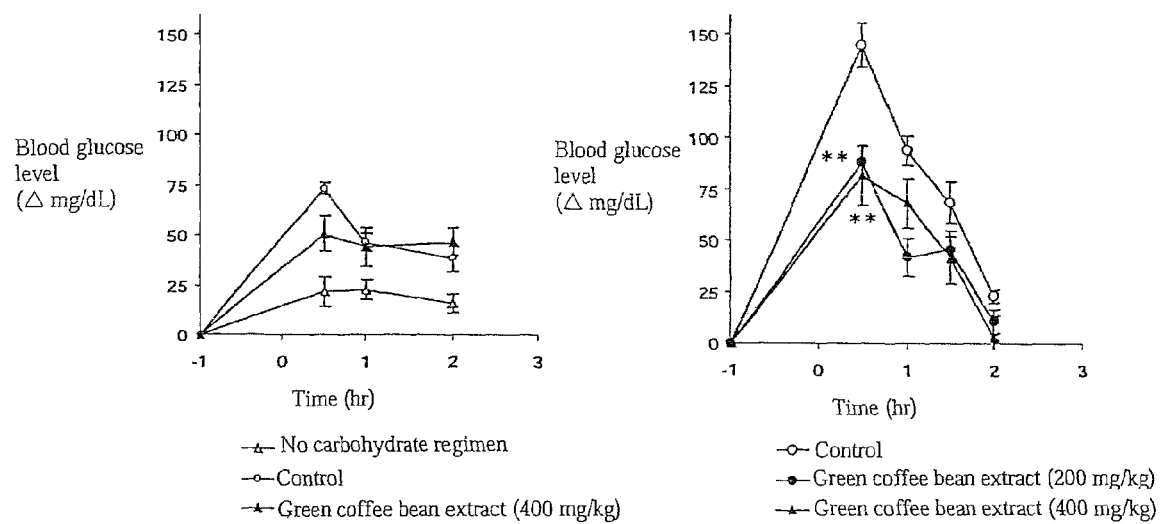
FIG. 12 is a graph showing the suppressive effect of the extract derived from the green coffee beans on the elevation of blood glucose levels when glucose or sucrose is taken into the body.

As shown in FIG. 12, administrating 400 mg/kg of the green coffee bean extract (Example) with a glucose load and 200 mg/kg of the green coffee bean extract (EXAMPLE) with sucrose load to the mice, respectively, suppresses the elevation of the blood glucose levels.

b. α-Glucosidase Inhibitory Activity (In Vivo):

In regard to the green coffee bean extract (Example) and its contained substances (chlorogenic acid, caffeine, and quinic acid), the α-glucosidase inhibitory activity which is a carbohydrate-degrading enzyme was evaluated by the in vivo experiment.

The test method is herein described. First of all, mix the acetone powder of the rat small intestine with the pH7.0. 0.1M phosphate buffer solution (product of SIGMA ADLRICH JAPAN K.K), which is approx. 10 times as much as the volume of the acetone powder, and obtain the enzyme liquid from the centrifuged supernatant. Use the 0.2 mM 4-methyl umbel phelyl-α-D-gluco-pyranoside (SIGMA ADLRICH JAPAN K.K) as a substrate. After dissolving each sample in the DMSO, prepare the two-fold dilution series with the 4% DMSO containing phosphate buffer solution. The diluted solution (50 μL/well) and buffered substrate (25 μL/well) are mixed in a microplate, and after preheating it at 37° C. for 10 minutes, add the enzyme liquid (25 μL/well) to induce the reaction at 37° C. for 30 minutes (final concentration of enzyme: 1 mg protein mL, final concentration of substrate: 0.05 mM). Then, add the 0.2M $Na_2CO_3$ (100 μL/well) to stop the reaction. Measure the fluorescence intensity (excitation wavelength: 366 nm, determined wavelength: 45 nm) using a microplate reader.

As shown in Chart 2, the green coffee bean extract (Example), chlorogenic acid and coffeic acid respectively indicate a strong inhibitory activity of α-glucosidase. However, caffeine and quinic acid does not indicate the inhibitory activity. The inhibitory activity of the green coffee bean extract (Example) is greater than that of the chlorogenic acid and coffeic acid.

CHART 2

| Class | $IC_{50}$ (μg/mL) |
| --- | --- |
| Green coffee bean extract: | 70 |
| Caffeine: | >1000 |
| Chlorogenic acid: | 100 |
| Coffeic acid: | 100 |
| Quinic acid: | >1000 |

(Blending Sample)

The blending samples of the dietetic composition in this invention are herein described. In the following samples, an hydroethanol extract derived from the defatted green coffee bean can also be used for the green coffee bean extract. Each blending example is also applicable for Invention 2 (a composition for suppressing the fat absorption), Invention 3 (a composition for inhibiting the pancreatic lipase activity), Invention 4 (a composition for promoting the carnitine palmitoyltransferase activity), and Invention 5 (a composition for inhibiting the α-glucosidase activity), respectively.

CHART 3

| Blending sample 1: Chewing gums | |
| --- | --- |
| Sugar: | 53.0 wt % |
| Gum base: | 20.0 |
| Glucose: | 10.0 |
| Starch syrup: | 16.0 |
| Aroma chemical: | 0.5 |
| Green coffee bean syrup (Dietetic composition): | 0.5 |
| | 100.0 wt % |

CHART 4

Blending sample 2: Gummies

| | |
|---|---|
| Reduced starch syrup: | 40.0 wt % |
| Granulated sugar: | 20.0 |
| Glucose sugar: | 20.0 |
| Gelatin: | 4.7 |
| Water: | 9.68 |
| Japanese plum juice: | 4.0 |
| Japanese plum flavor: | 0.6 |
| Pigment: | 0.02 |
| Green coffee bean syrup (Dietetic composition): | 1.05 |
| | 100.0 wt % |

CHART 5

Blending example 3: Candies

| | |
|---|---|
| Sugar: | 50.0 wt % |
| Starch syrup: | 33.0 |
| Water: | 14.4 |
| Organic acid: | 2.0 |
| Aroma chemical: | 0.2 |
| Green coffee bean extract (Dietetic composition): | 0.4 |
| | 100.0 wt % |

CHART 6

Blending example 4: Yogurts (Natural/Firm)

| | |
|---|---|
| Milk: | 41.5 wt % |
| Skimmed milk: | 5.8 |
| Sugar: | 8.0 |
| Agar-agar: | 0.15 |
| Gelatin: | 0.1 |
| Lactobacillus: | 0.005 |
| Green coffee bean extract (Dietetic composition): | 0.4 |
| Aroma chemical: | Trace amount |
| Water: | Rest |
| | 100.0 wt % |

CHART 7

Blending sample 5: Soft capsules

| | |
|---|---|
| Sprouted brown rice oil: | 87.0 wt % |
| Emulsifying agent: | 12.0 |
| Green coffee bean extract (Dietetic composition): | 1.0 |
| | 100.0 wt % |

CHART 8

Blending sample 6: Coffee drinks (Liquid type)

| | |
|---|---|
| Roasted coffee bean: | 6.0 wt % |
| Sugar: | 6.0 |
| Baking soda: | 0.2 |
| Emulsifying agent: | 0.15 |
| Green coffee bean extract (Dietetic composition): | 1.0 |
| Water: | Rest |
| | 100.0 wt % |

CHART 9

Blending sample 7: Coffee drinks (Powder type)

| | |
|---|---|
| Instant coffee granule: | 90.0 wt % |
| Skimmed milk: | 7.0 |
| Green coffee bean extract (Dietetic composition): | 3.0 |
| | 100.0 wt % |

CHART 10

Blending sample 8: Soft drinks

| | |
|---|---|
| High fructose corn syrup: | 30.0 wt % |
| Emulsifying agent: | 0.5 |
| Green coffee bean extract (Dietetic composition): | 0.05 |
| Aroma chemical: | Appropriate amount |
| Distilled water: | Rest |
| | 100.0 wt % |

CHART 11

Blending sample 11: Tablets

| | |
|---|---|
| Lactose: | 54.0 wt % |
| Crystalline cellulose: | 30.0 |
| Starch splitting product: | 10.0 |
| Glycerin fatty acid ester: | 5.0 |
| Green coffee bean extract (Dietetic composition): | 1.0 |
| | 100.0 wt % |

CHART 12

Blending sample 10: Tablet-shaped sweets

| | |
|---|---|
| Sugar: | 76.4 wt % |
| Glucose: | 19.0 |
| Glycerin fatty acid ester: | 0.2 |
| Green coffee bean extract (Dietetic composition): | 0.5 |
| Distilled water: | 3.9 |
| | 100.0 wt % |

CHART 13

Blending sample: Cosmetic creams

| | |
|---|---|
| Squalene: | 20.0 wt % |
| Bees wax: | 5.0 |
| Distilled jojoba oil: | 5.0 |
| Glycerin: | 5.0 |
| Glycerin monostearate: | 2.0 |
| Polyoxyethylene (20) sorbitan-monostearate: | 2.0 |
| Green coffee bean extract (Dietetic composition): | 2.0 |
| Food preservative: | Appropriate amount |
| Aroma chemical: | Appropriate amount |
| Distilled water: | Rest |
| | 100.0 wt % |

CHART 14

Blending example 12: Skin lotions

| | |
|---|---|
| Ethanol: | 5.0 wt % |
| Glycerin: | 2.0 |
| 1,3-butylene glycol: | 2.0 |

CHART 14-continued

Blending example 12: Skin lotions

| | |
|---|---|
| Polyethylene oleyl ether: | 0.5 |
| Sodium citrate: | 0.1 |
| Citric acid: | 0.1 |
| Green coffee bean extract (Dietetic composition): | 0.1 |
| Distilled water: | Rest |
| | 100.0 wt % |

CHART 15

Blending example 13: Body gel

| | |
|---|---|
| Macadamia nut oil: | 2.0 wt % |
| Octyl decyl myristate: | 10.0 |
| Methylphenyl polysiloxane: | 5.0 |
| Behenyl alcohol: | 3.0 |
| Stearic acid: | 3.0 |
| Batyl alcohol: | 1.0 |
| Glycel monostearate: | 1.0 |
| Tetra oleic acid polyoxyethylene sorbit: | 2.0 |
| Hydrogenated soybean phosphatide: | 1.0 |
| Ceramide: | 0.1 |
| Retinol palmitate: | 0.1 |
| Preservative: | Appropriate amount |
| *Centella asiatica* extract: | 1.0 |
| Green coffee bean extract (Dietetic composition): | 1.0 |
| 1,3-butylene glycol: | 5.0 |
| Distilled water: | Rest |
| | 100.0 wt % |

CHART 16

Blending example 14: Cosmetic emulsion

| | |
|---|---|
| Squalene: | 4.0 wt % |
| Vaseline: | 2.5 |
| Cetanol: | 2.0 |
| Glycerin: | 2.0 |
| Oleophilic glycerin monostearate: | 1.0 |
| Stearic acid: | 1.0 |
| L-arginine: | 1.0 |
| Green coffee bean extract (Dietetic composition): | 0.5 |
| Potassium hydroxide: | 0.1 |
| Aroma chemical: | Trace amount |
| Distilled water: | Rest |
| | 100.0 wt % |

CHART 17

Blending example 15: Bath agent (liquid type)

| | |
|---|---|
| Propylene glycol: | 50.0 wt % |
| Ethanol: | 20.0 |
| Sodium sulphate: | 5.0 |
| Green coffee bean extract (Dietetic composition): | 0.5 |
| Lanoline: | 0.5 |
| Avocado oil agent: | 0.5 |
| Pigment: | 1.5 |
| Aroma chemical: | 22.0 |
| | 100.0 wt % |

INDUSTRIAL APPLICABILITY

As described above, this invention provides the following excellent effects.

(a) Excellent dietetic effect can be obtained by taking a highly safe extract derived from the green coffee beans, and which contributes the prevention and treatment of life-style diseases such as diabetes or the like.

(b) The safe extract derived from the green coffee beans is usable as a material for foods, drinks, drugs or the like.

The invention claimed is:

1. A method for promoting carnitine palmitoyltransferase activity in a person suffering from obesity for the purpose of enhancing fat burning in the person, the method comprising orally administering to said person 0.5 mg to 5,000 mg per day of a green coffee bean extract; wherein the green coffee bean extract is obtained by defatting a green coffee bean with N-hexane and extracting the defatted green coffee bean with 40 to 90% ethanol to obtain a hydroethanolic extract of the defatted green coffee.

2. The method of claim 1, wherein the administering step includes further administering to said person one or more substances selected from the group consisting of *Salacia* extract, evening primrose extract, sesamin and *Garcinia*.

3. The method of claim 1, wherein the administering step further comprises administering to said person, one or more substances selected from the group consisting of among *Gymnema sylvestre*, mulberry leaf, guava leaf, white kidney bean, glucomannan, yacon, chia seed, fenugreek, wheat amylase inhibitor, balsam, pear, conjugated linoleic acid, L-carnitine, *Coleus forskohlli*, yerba mate, *Astibe thunbergii*, *Citrus aurantium*, paprika, capsiate, *Cassia polyphenol, Malus* extract, green tea extract, green tea polyphenol, soybean isoflavone, purple rice extract, chitosan and raspberry ketone.

4. The method of claim 1, wherein the green coffee bean extract is contained in a composition.

5. The method of claim 4 wherein the composition is a confectionary, a food, a beverage or a seasoning.

6. The method of claim 5, wherein the composition is a confectionary selected from the group consisting of chewing gum, candy, caramel, chocolate, cookies, jelly, gummies and tablet-shaped sweets.

7. The method of claim 5, wherein the composition is a food selected from the group consisting of noodles, ice cream, yogurt and soup.

8. The method of claim 5, wherein the composition is a seasoning selected from the group consisting of fermented bean paste and soy sauce.

9. The method of claim 5, wherein the composition is a beverage selected from the group consisting of juice, coffee, black tea, green tea and a carbonated drink.

10. The method of claim 4 wherein the composition is a medicine and wherein the medicine is in the form of a tablet, powder, granule or liquid.

11. The method of claim 10, wherein the medicine comprises vehicles, binders or disintegrating agents.

12. The method of claim 10, wherein the medicine comprises a vehicle selected from the group consisting of glucose, sucrose, white sugar, sodium chloride, starch, calcium carbonate, kaolin, crystalline cellulose, cacao oil, hydrogenated vegetable oil and talc.

13. The method of claim 10, wherein the medicine comprises a binder selected from the group consisting of distilled water, saline solution, ethanol in water, ethanolic solution, syrup, dextrose in water, starch solution, gelatin solution, carboxymethyl cellulose, potassium phosphate and polyvinyl pyrrolidone.

14. The method of claim 10, wherein the medicine comprises a disintegrating agent selected from the group consisting of sodium alginate, agar-agar, sodium hydrogen carbonate, sodium lauryl sulphate, stearic acid monoglyceride, starch, lactose, powdered aracia, gelatin and ethanol.

15. The method of claim 5, wherein orally administering comprises orally administering to said person 0.5 mg to 3,000 mg per day of the green coffee bean extract.

16. The method of claim 5, wherein the green coffee bean extract contains chlorogenic acid and caffeine.

17. The method of claim 5, wherein extracting with 40 to 90% ethanol is carried out at a temperature range of 20 to 80° C.

18. The method of claim 5, wherein extracting with 40 to 90% ethanol is carried out at a temperature range of 40 to 50° C.

19. The method of claim 5, wherein extracting with 40 to 90% ethanol comprises soaking extraction, continuous extraction or countercurrent extraction.

* * * * *